(12) United States Patent
Nielsen et al.

(10) Patent No.: US 9,212,390 B2
(45) Date of Patent: Dec. 15, 2015

(54) IN SITU HYBRIDIZATION METHOD AND BUFFER

(75) Inventors: Boye Schnack Nielsen, Copenhagen (DK); Stine Jørgensen, Copenhagen (DK); Jan Skouv, Espergaerde (DK); Adam Baker, Vedbaek (DK); Søren Møller, Holte (DK)

(73) Assignee: EXIQON A/S, Vedbaek (DK)

( * ) Notice: Subject to any disclaimer, the term of this patent is extended or adjusted under 35 U.S.C. 154(b) by 304 days.

(21) Appl. No.: 13/695,427

(22) PCT Filed: Apr. 28, 2011

(86) PCT No.: PCT/DK2011/050136
§ 371 (c)(1),
(2), (4) Date: Mar. 14, 2013

(87) PCT Pub. No.: WO2011/134474
PCT Pub. Date: Nov. 3, 2011

(65) Prior Publication Data
US 2013/0164750 A1 Jun. 27, 2013

Related U.S. Application Data

(60) Provisional application No. 61/343,596, filed on Apr. 30, 2010.

(51) Int. Cl.
*C12Q 1/68* (2006.01)
*C07H 21/00* (2006.01)

(52) U.S. Cl.
CPC ............ *C12Q 1/6841* (2013.01); *C12Q 1/6876* (2013.01); *C12Q 1/6886* (2013.01); *C12Q 2600/118* (2013.01); *C12Q 2600/158* (2013.01); *C12Q 2600/178* (2013.01)

(58) Field of Classification Search
CPC ....... C12Q 1/68; C12Q 1/6813; C12Q 1/6841
USPC .......................................... 435/6.1; 536/22.1
See application file for complete search history.

(56) References Cited

U.S. PATENT DOCUMENTS

| | | | |
|---|---|---|---|
| 5,521,061 A | 5/1996 | Bresser et al. | |
| 5,693,473 A * | 12/1997 | Shattuck-Eidens et al. . | 435/6.12 |
| 5,750,340 A | 5/1998 | Kim et al. | |
| 6,043,060 A | 3/2000 | Imanishi | |
| 6,268,490 B1 | 7/2001 | Imanishi et al. | |
| 7,105,294 B2 | 9/2006 | Van Dongen et al. | |
| 7,521,479 B2 | 4/2009 | Merril et al. | |
| 2002/0150631 A1 | 10/2002 | Merril et al. | |
| 2004/0043383 A1 | 3/2004 | Van Dongen et al. | |
| 2009/0130673 A1 | 5/2009 | Shah et al. | |
| 2011/0183331 A1 * | 7/2011 | Doi et al. ...................... | 435/6.11 |

FOREIGN PATENT DOCUMENTS

| | | |
|---|---|---|
| EP | 0 357 436 A2 | 3/1990 |
| EP | 0 432 221 B1 | 5/1997 |
| EP | 0 440 749 B1 | 5/1997 |
| WO | 96/31626 A1 | 10/1996 |
| WO | 96/36734 A1 | 11/1996 |
| WO | 98/39352 A1 | 9/1998 |
| WO | 99/14226 A2 | 3/1999 |
| WO | 99/60163 A1 | 11/1999 |
| WO | 00/56746 A2 | 9/2000 |
| WO | 00/56748 A1 | 9/2000 |
| WO | 00/66604 A2 | 11/2000 |
| WO | 01/00641 A1 | 1/2001 |
| WO | 01/07455 A1 | 2/2001 |
| WO | 03/020739 A2 | 3/2003 |
| WO | 2006/069584 A2 | 7/2006 |
| WO | 2007/073737 A1 | 7/2007 |
| WO | 2007/112753 A2 | 10/2007 |
| WO | WO 2009/142214 * | 11/2009 |

OTHER PUBLICATIONS

Ahern. Biochemical, Reagent Kits Offer Scientists Good Return on Investment. The Scientist 9(15) : 20 (1995).*
Kloosterman et al.,In situ detection of miRNAs in animal embryos using LNA-modified oligonucleotide probes. Nature Methods 3 (1) : 27 (2006).*
Jorgensen et al, "Robust one-day in situ hybridization protocol for detection of microRNAs in paraffin samples using LNA probes", Methods : A Companion to Methods in Enzymology, Academic Press Inc., New York, NY, US, vol. 52, No. 4, Dec. 1, 2010, pp. 375-381, XP027493680, ISSN: 1046-2023, DOI: D01:10.1016/J.YMETH.2010.07.002 [retrieved on Jul. 16, 2010].
Kloosterman et al, "In situ detection of miRNAs in animal embryos using LNA-modified oligonucleotide probes", Nature Methods, Nature Publishing Group, GB, vol. 3, No. 1, Jan. 1, 2006, pp. 27-29, XP008085404, ISSN: 1548-7091, DOI: D01:10.1038/NMETH843.
Nielsen et al, "High levels of microRNA-21 in the stroma of colorectal cancers predict short disease-free survival in stage II colon cancer patients", Clinical & Experimental Metastasis Official Journal of Themetastasis Research Society, Kluwer Academic Publishers, DO, vol. 28, No. 1, Oct. 31, 2010, pp. 27-38, XP019867526, ISSN: 1573-7276, DOI: D01:10.1007/S10585-010-9355-7.

(Continued)

*Primary Examiner* — Ethan C Whisenant
(74) *Attorney, Agent, or Firm* — McDonnell Boehnen Hulbert & Berghoff LLP

(57) ABSTRACT

An improved method of in situ hybridization which relies on an improved formulation of the in situ hybridization buffer is described. In at least some formulations the buffer are non-toxic. The combination of Locked Nucleic Acid (LNA) comprising ISH probes and the improved ISH buffer are useful for detection of small non-coding RNA as well as in the manufacturing of ISH kits directed to the detection of such small non-coding RNA. Further disclosed is a method of semi-quantitative ISH and demonstration of the semi-quantitative ISHs diagnostic potential.

8 Claims, 12 Drawing Sheets

(56) References Cited

OTHER PUBLICATIONS

Figure 1:
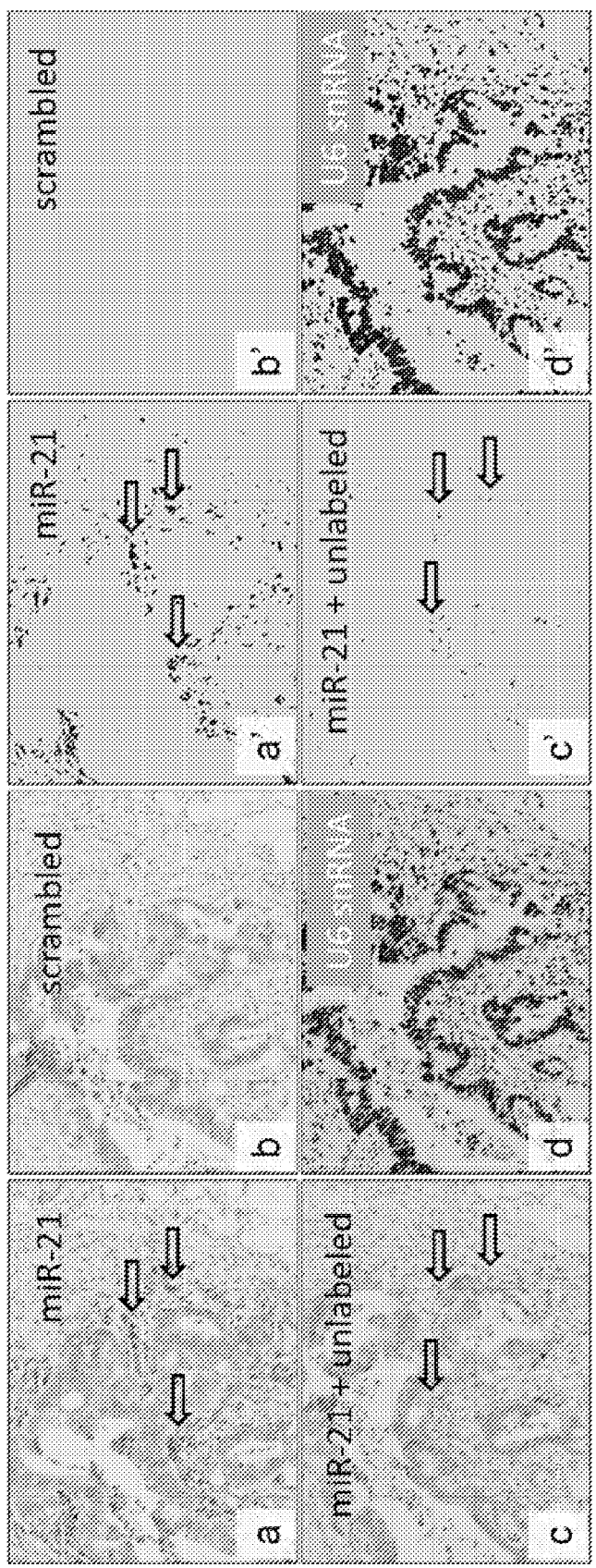

Oliva et al, "Fluorescene In Situ Hybridization Method for Co-Localiation of MRNA and GFP", Biotechniques, vol. 31, No. 1, Jul. 1, 2001, pp. 74-81, XP008023483,ISSN: 0736-6205 the whole document, "Amplified Fluorescence mRNA In Situ Hybridization".

Ryan et al, "MicroRNAs of the mammalian eye display distinct and overlapping tissue specificity", Molecular Vision, Molecular Vision, SN, Atlanta, vol. 12, Jan. 1, 2006, pp. 1175-1184, XP002536158, ISSN: 1090-0535 [retrieved on Oct. 17, 2006].

Thomas et al, "Demonstration of MRNA Using Digoxigenin Labelled Oligonucleotide Probes for In Situ Hybridisation in Formamide Free Conditions", Journal of Clinical Pathology, BMJ Publishing Group, GB, vol. 46, No. 2, Jan. 1, 1993, pp. 171-174, XP009012568, ISSN: 0021-9746, DOI: D01:10.1136/JCP.46.2.171.

Yamamichi et al, "Locked Nucleic Acid In situ Hybridization Analysis of miR-21 Expression during Colorectal Cancer Development", Clinical Cancer Research, vol. 15, No. 12, Jun. 15, 2009, pp. 4009-4016, XP55002619, ISSN: 1078-0432, DOI: 10.1158/1078-0432. CCR-08-3257.

Ahlfen et al., Determinants of RNA quality from FFPE samples, PLoS One, Jan. 2007; 2(12): e1261.

Barbarotto et al , MicroRNAs and cancer: profile, profile, profile, Int J Cancer, Mar. 2008; 122(5): 969-77.

Bartels, Mini-Reviews: MicroRNAs: Novel Biomarkers for Human Cancer, Clin. Chem., Apr. 2009; 55: 623-631.

Ke et al., MicroRNAs: key participants in gene regulatory networks, Curr Opin Chem Biol, Aug. 2003; 7(4): 516-23.

Kibbe, OligoCalc: an online oligonucleotide properties calculator, Nucleic Acids Res., Jul. 2007; 35: W43-W46.

Mynster et al, The impact of storage time of transfused blood on postoperative infectious complications in rectal cancer surgery. Danish RANX05 Colorectal Cancer Study Group, Scand J Gastroenterol, Feb. 2000; 35(2): 212-7.

Santalucia Jr., Biochemistry: A unified view of polymer, dumbbell, and oligonucleotide DNA nearest-neighbor thermodynamics, PNAS, Feb. 1998; 95: 1460-1465.

Schetter et al, MicroRNA expression profiles associated with prognosis and therapeutic outcome in colon adenocarcinoma, JAMA, Jan. 2008; 299(4): 425-36.

Wienholds et al., Reports: MicroRNA Expression in Zebrafish Embryonic Development, Science, Jul. 2005; 309: 310-311.

\* cited by examiner

IN SITU HYBRIDIZATION METHOD AND BUFFER

This application is the National Stage of International Application No. PCT/DK2011/050136, filed Apr. 28, 2011, which claims the benefit of U.S. Provisional Application No. 61/343,596, filed Apr. 30, 2010.

FIELD OF THE INVENTION

The present invention relates to the field of in situ hybridization (ISH) on tissue sections. In particular the invention relates to an improved method of in situ hybridization which relies on an improved formulation of the in situ hybridization buffer, at least some of which formulations are non-toxic. Together with Locked Nucleic Acid (LNA) comprising ISH probes the improved ISH buffer are useful for detection of specific nucleic acid molecules such as mRNA, rRNA and in particularly small non-coding RNA as well as in the manufacturing of ISH kits directed to the detection of such small non-coding RNA. Further disclosed is a method of semi-quantitative ISH and demonstration of the semi-quantitative ISHs diagnostic potential.

BACKGROUND OF THE INVENTION

In situ hybridization (ISH) of tissue samples is a nucleic acid hybridization technique used to investigate and localize target nucleic acids in morphologically preserved structures, e.g. within a cell, a tissue, a nucleus or a chromosome.

Today most pathological samples are routinely fixed and paraffin-embedded to allow for histological analysis and for archival storage. Formalin fixation and paraffin embedding are estimated to be used in over 90% of specimens prepared by clinical labs in preparation of specimens for histological diagnosis. Archives of well-annotated formalin-fixed, paraffin-embedded (FFPE) tissue specimens are invaluable resources for retrospective studies of human diseases, however the FFPE procedure as well as the storage of the samples is known to introduce adverse effects on the RNA quality (Ahlfen et al. (2007) PLoS ONE 2(12): e1261). Formalin fixation proceeds relatively slowly, a fixation-time of 16-24 h is conventional, and results in a relatively slow quenching of the endogenous RNases which invariably cause some RNA degradation. However, numerous studies have shown the formalin fixation as well as other aldehyde-based fixations such as paraformaldehyde- and glutaraldehyde-fixed specimens can be used for in situ hybridization of RNA.

Several methods for ISH on formalin-fixed, paraffin-embedded tissue have been described; interestingly all protocols are comprised with a hybridization step in a formamide comprising hybridization buffer. Formamide is also mentioned as the component in the hybridization mix in EP 440.749 B1, EP 432.221 B1, U.S. Pat. No. 5,521,061 and U.S. Pat. No. 5,750, 340 as well as in the papers on ISH prepared on archival FFPE specimens known to the inventor. However importantly, formamide is characterized as a teratogenic substance that should be avoided.

Recently, a large number of small non-coding RNA genes have been identified and designated as microRNAs (miRNAs or miRs) (for review, see Ke et al. 2003, Curr. Opin. Chem. Biol. 7:516-523). They are typically 17-24 nucleotides (nt) long RNAs that are processed from longer endogenous hairpin transcripts. To date more than 6000 miRs have been identified in humans, worms, fruit flies and plants according to the miR registry database release 11.0 in April 2008, hosted by Sanger Institute, UK.

The importance of microRNAs in cancer is highlighted in a recent article (Barbarotto et al 2008 Int. J. Cancer. 122:969-977), which summarizes the main paradigms for the miRNA involvement in human cancers: Thus, "(i) miRNAs are altered in every type of analyzed human cancer; (ii) miRNAs act as oncogenes and tumor suppressors; (iii) miRNAs alterations may cause cancer predisposition; (iv) miRNAs profiling is a new diagnostic tool for cancer patients and (v) miRNA profiling represents prognostic tools for cancer patients.". Accordingly, methods in particularly ISH methods that can be used for localization of expression and quantification of microRNAs in specific cells and tissues from cancer patients are needed.

Some further of the recent attention paid to small RNAs in the size range of 17 to 25 nt is due to the phenomenon RNA interference (RNAi). RNAi is the mechanism in which double-stranded RNA leads to the degradation of any RNA that is homologous RNAi relies on a complex and ancient cellular mechanism that has probably evolved for protection against viral attack and mobile genetic elements. A crucial step in the RNAi mechanism is the generation of short interfering RNAs (siRNAs) which are double-stranded RNAs that are about 22 nt long each.

Quantification of microRNAs and siRNAs by ISH procedures is very challenging due to the small size of the RNAs. Furthermore a high specificity is required since different small RNAs may only differ with respect to a single nucleotide, but present day ISH-protocols for FFPE samples often suffer by lack of sensitivity or high background levels.

Thus an improved method of detecting small non-coding RNAs by ISH in archival paraffin embedded specimens is highly needed.

The present invention provides an improved, robust and fast ISH method for detection of non-coding RNAs in FFPE-samples. The method avoid use of the teratogenic formamide while providing even better ISH-results than obtained with standard formamide comprising hybridization buffers. Furthermore the method has the advantage that it can be used for quantification of small non-coding RNAs by ISH in archival FFPE-samples.

SUMMARY OF THE INVENTION

Prior to the present invention, the present inventors believed that formamide was an indispensable component of a successful ISH hybridization mix.

However, the present inventors, surprisingly, observed that formamide may be substituted by certain chaotropic substances such as, for example, urea and guanidine hydrochloride to obtain even better ISH-results than obtained with standard formamide comprising hybridization buffers.

Thus, in a first aspect, the invention pertains to a method for detection of nucleic acid molecules comprising a contiguous a nucleotide sequence such as mRNA by in situ hybridisation in fixed cellular specimens comprising of a hybridization step which is performed in a formamide-free, hybridization buffer that comprises a chaotropic component selected from the group of urea, salts of guanidinium or guanidine and a mixture of two or more members of the group.

In one preferred embodiment, the invention pertains to a method for detection of small, non-coding RNAs by in situ hybridisation in fixed cellular specimens comprising of a hybridization step which is performed in a formamide-free, hybridization buffer that comprises a chaotropic component selected from the group of urea, salts of guanidinium or guanidine and a mixture of two or more members of the group.

In a further preferred embodiment, the improved, formamide-free, hybridization buffer is used of detecting nucleic acid molecules in standard formalin-fixed and paraffin-embedded (FFPE) tissue sections or in frozen (cryostat) tissue sections.

In a second aspect the invention provide an improved, formamide-free, hybridization buffer for the use of detecting nucleic acid molecules comprising a contiguous a nucleotide sequence such as mRNA, rRNA or small non-coding RNAs in tissue sections with probes, in particularly LNA-probes, by in situ hybridization, the buffer comprise 0.5 to 5 M of a chaotropic component selected from the group comprised of urea and salts of guanidinium (or guanidine) or a mixture of two or more members of the group.

In a preferred embodiment of the invention an improved, formamide-free, hybridization buffer for detecting nucleic acid molecules in standard formalin-fixed and paraffin-embedded (FFPE) tissue sections is provided.

According to the present invention, there is also provided a kit for detection of at least one small non-coding RNAs in standard formalin-fixed and paraffin-embedded (FFPE) tissue by in situ hybridization, said kit comprise the improved, formamide-free, hybridization buffer and least one LNA-probe optimized for the specific detection of said one small non-coding RNA.

A further advantage of the herein disclosed method is its robustness and low variance allowing it to be used for semi-quantitative in situ hybridization allowing for miRNA-associated diagnostics such as for a method of estimating/evaluating disease-free survival in stage II colon cancer comprising:

a) determining the relative level of miR-21 in at least one representative tissue section from a stage II colon cancer of said patient determined by the method of claim 7, b) comparing the level of miR-21 in the patient to a set of relative levels of miR-21 obtained by the method of claim 7 from a reference panel of stage II colon cancer samples obtained from a reference panel of patients with known disease history, c) grouping the reference panel in tertiles according to the relative level of miR-21 determined by the method of claim 7; and d) taking the miR-21 level of said at least one representative tissue section from a stage II colon tumor from said patient that falls within the miR-21 level of the upper (high expressing) tertile as indicative of an increased likelihood of short disease-free survival, and taking a miR-21 level of said at least one representative tissue section from a stage II colon tumor from said patient that falls within the miR-21 level of the lower (low expressing) tertile as indicative of an increased likelihood of long disease-free survival.

DEFINITIONS

Prior to a discussion of the detailed embodiments of the invention is provided a definition of specific terms related to the main aspects of the invention.

Small, Non-Coding RNAs

The terms "miRNA" and "microRNA" refer to 17-25 nt non-coding RNAs. They are processed from longer (ca 75 nt) hairpin-like precursors termed pre-miRNAs. MicroRNAs assemble in complexes termed miRNPs and recognize their targets by antisense complementarity. If the microRNAs match 100% to their target, i.e. the complementarity is complete, the target mRNA is most probably cleaved, and the miRNA acts like a siRNA. If the match is incomplete, i.e. the complementarity is partial, then the translation of the target mRNA is most probably blocked.

The terms "Small interfering RNAs" or "siRNAs" refer to 21-25 nt RNAs derived from processing of linear double-stranded RNA. siRNAs assemble in complexes termed RISC (RNA-induced silencing complex) and target homologous complementary RNA sequences for endonucleolytic cleavage. Synthetic siRNAs also recruit RISCs and are capable of cleaving homologous complementary RNA sequences.

The term "RNA interference" (RNAi) refers to a phenomenon where double-stranded RNA homologous to a target mRNA leads to degradation of the targeted mRNA. More broadly defined as degradation of target mRNAs by fully or partly complementary siRNAs. MicroRNAs (miRNA or miR) are an abundant class of short endogenous RNAs that act as posttranscriptional regulators of gene expression by base-pairing with their target mRNAs.

The term "messenger RNA" or mRNA is used as in the art to describe the RNA-type that is transcribed from a DNA template, and which carries the coding information to the sites of protein synthesis, the ribosomes.

The term "ribosomal RNA" (rRNA) refers to the RNA component of the ribosome.

In Situ Hybridization

"In situ hybridization" is a technique providing the specific detection of nucleic acids molecules within individual cells, tissue sections or even whole mounts (i.e. whole organisms, embryons, organs etc.) typically deposited on a solid support, in floating sections or immersed.

Cellular Specimen

The term "cellular specimen" denotes a sample of cells. It include, but are not limited to, a tissue section, specific types of cell isolated from tissue sections (e.g. by laser capture microdissection), a cytospin, a cell smear, a sample of cells obtained from a cell growth medium or a mixture thereof. The terms encompass samples regardless of their physical condition; stated differently, the terms do not exclude material by virtue of the physical state (such as, but not limited to, being frozen or stained or otherwise treated).

Fixed Cellular Specimen.

By the terms "fixed" or "fixed cellular specimen" is referred to the process wherein cellular specimens are preserved while maintaining the histological structure of the specimen. Fixation of cellular specimens can be accomplished by various cross-linking fixatives to form cross-links in tissue, by alcohol and acetone to coagulate and dehydrate the specimen, or by cryopreservation. Cross-linking fixatives include formaldehyde, glutaraldehyde, paraformaldehyde, ethyldimethyl-aminopropyl-carbodiimide, and dimethyl-silserimidate.

By the terms "aldehyde-fixed" and "aldehyde-fixed cellular specimen" is referred to the process wherein cellular specimens are fixed by aldehyde fixatives such as formalin (formaldehyde), glutaraldehyde or paraformaldehyde.

FFPE Specimen shall mean formalin-fixed, paraffin-embedded specimen. FFPE specimen (often referred to as archival FFPE specimen, routinely-fixed specimen, FFPEs or FFPE-blocks) is routinely processed at the hospitals.

Routinely-Fixed shall mean fixation according to standards at pathology departments typically using 1-3 days fixation of clinical tissue specimens in 10% neutral-buffered formalin (i.e. 4% (0.32 M) formaldehyde in phosphate-buffered saline, pH around 7) at room temperature. New and fast fixation methods, eg. involving micro-wave-based fixation, is becoming routine and thus comprised by thid definition.

Routinely-Fixed, Paraffin-Embedded Specimen shall mean any piece of tissue of eukaryotic origin, taken by dissection, biopsy, blood sample, etc., which is first spatially immobilized by cross-linking its macromolecules in a locked positions and then embedded in paraffin to prevent degeneration. Such fixed, paraffin-embedded specimen can be stored at room temperature for years and sections from them can be made with a thickness typically in the range of 3-6 μm can be cut and transferred to solid support for downstream molecular, histological, pathological and cytological evaluation. For the avoidance of doubt tissue comprised by this definition includes FFPE specimens.

Chaotropic Component

In the present context the term "chaotropic component" refers to a "chaotropic agent", also known as a "chaotropic reagent" or a "chaotrope", which is any chemical substance which disturbs the ordered structure of liquid water. A chaotropic agent also disrupts the three dimensional structure in macromolecules including but not limited to proteins, DNA, or RNA. Preferred chaotropic salts are, guanidinium thiocyanate, guanidinium isothiocyanate or guanidinium hydrochloride. Another preferred chaotropic agent is urea.

Salts of Guanidinium or Guanidine includes but are is not limited to guanidinium thiocyanate, guanidinium isothiocyanate or guanidinium hydrochloride.

Nucleic Acids Molecules

In the present context "nucleic acids molecules" refer to nucleic acid polymers. such as RNA, DNA or polymers comprising or consisting of nucleotide analogues (such as LNA oligonucleotides).

Hybridization

"Hybridization" refers to the bonding of two complementary single stranded nucleic acid polymers, the (such as oligonucleotides), such as RNA, DNA or polymers comprising or consisting of nucleotide analogues (such as LNA oligonucleotides). Hybridisation is highly specific, and may be controlled by regulation of the concentration of salts and temperature. Hybridisation occurs between complementary sequences, but may also occur between sequences which comprise some mismatches. The oligonucleotides used in the methods of the present invention may, therefore be 100% complementary to the target molecule. Alternatively, in the oligonucleotides may comprise mismatches.

Tm

The term "Tm" or "melting temperature" of an oligonucleotide measures the stability of a DNA duplex formed between the oligonucleotide and its perfect complement DNA strand. Tm is defined as the temperature at which 50% of the DNA duplexes formed between the oligonucleotide and its perfect complement DNA strand are dissociated into single strands. The length and nucleotide composition, such as the sequence of nucleotides and content of G and C nucleotides, of the oligonucleotide are important factors affecting Tm. Substitution of the normal A, G, C and T nucleotides with the corresponding LNA molecules in an oligonucleotide increases Tm. Similary, hybridisation conditions defined by salt concentration, oligonucleotide concentration, and the presence of denaturants (such as formamide or DMSO) affects Tm. Those skilled in the art of molecular biology know that several useful formulas for calculation of theoretical Tm's have been developed to evaluate the Tm of an oligonucleotide for PCR, Southern and Northern blots, and in situ hybridization. Examples of Tm calculators are OligoCalc (W. A. Kibbe (2007) Nucleic Acids Res Volume 35, Web Server issue W43-W46) and LNA Probe Tm Predictor at http://www.exiqon.com.

Probe

In typical embodiments herein, a "probe" is a capture agent that is directed to a polynucleotide e.g. an microRNA. Typically the probe is a polynucleotide itself. The polynucleotide that a probe is directed to is referenced herein as "target".

If a polynucleotide, e.g. a probe, is "directed to" or "specific for" a target, the polynucleotide has a sequence that is complementary to a sequence in that target and will specifically bind (i.e. hybridize) to that target under hybridization conditions. The hybridization conditions typically are selected to produce binding pairs of nucleic acids, e.g., probes and targets, of sufficient complementarity to provide for the desired level of specificity in the assay while being incompatible to the formation of binding pairs between binding members of insufficient complementarity to provide for the desired specificity. Such hybridization conditions are typically known in the art. Examples of such appropriate hybridization conditions are also disclosed herein for hybridization of a probe to a to a target nucleic acid within individual cells or tissue sections deposited on a solid support. The target will typically be a miRNA for embodiments discussed herein.

Locked Nucleic Acid (LNA)

By "locked nucleic acid", "LNA" is meant a nucleoside or nucleotide analogue that includes at least one LNA monomer. By "LNA monomer" or "LNA nucleoside" or "LNA nucleotide" is referred to a nucleoside or nucleotide analogue wherein the ribose part is modified to form a bicyclic structure as disclosed in PCT Publication WO 99/14226.

LNA monomers as disclosed in PCT Publication WO 99/14226 are in general particularly desirable modified nucleic acids for incorporation into an oligonucleotide to improve its functionality as a probe. Additionally, the nucleic acids may be modified at either the 3' and/or 5' end by any type of modification known in the art. For example, either or both ends may be labeled with a Digoxigenin moiety. Desirable LNA monomers, LNA nucleosides and LNA nucleotides and their method of synthesis also are disclosed in U.S. Pat. No. 6,043,060, U.S. Pat. No. 6,268,490, PCT Publications WO 01/07455, WO 01/00641, WO 98/39352, WO 00/56746, WO 00/56748, WO 00/66604 and WO 03/020739 and elsewhere. Preferred LNA monomers, also referred to as "oxy-LNA", are LNAs wherein the bridge between R4* and R2* as shown in formula (I) of WO 99/14226 and also shown below, together designate —CH2-O— or —CH2-CH2-O—.

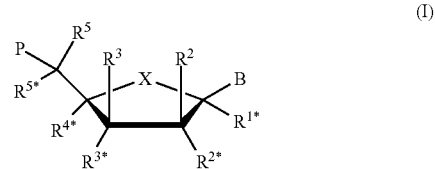

(I)

Oligo

By "oligonucleotide," "oligomer," or "oligo" is meant a successive chain of monomers (e.g., glycosides of heterocyclic bases) connected via internucleoside linkages. An oligo that includes at least one LNA monomer may be referred to as "LNA".

In the present context, the terms "nucleobase" covers naturally occurring nucleobases as well as non-naturally occurring nucleobases. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, and 5-methylcytosine.

In the nucleic acid sequences described herein LNA monomers are depicted in capitals (T, A, G) and DNA monomers in lower case (t, a, c, g). Modified LNA monomers include 5' methyl cytosine shown as capital C.

Embodiments of the present invention is described below, by way of examples only.

DETAILED DISCLOSURE OF THE INVENTION

The present invention provides a method for the detection of nucleic acids within individual cells or tissue sections deposited on a solid support.

As discussed previously, the present inventors initially considered formamide to be an indispensable component of a successful ISH hybridization mix. However confronted with the generally accepted genotoxic effects of formamide (EU Dangerous Substances Directive (67/548/EEC)) they searched for alternatives.

Much to their surprise they found that substituting formamide with a chaotropic component selected from the group of urea, salts of guanidinium or guanidine in the ISH hybridization mix paved the way to an improved method for detection of small, non-coding RNAs by in situ hybridisation of fixed cellular specimens. One particularly preferred type of small, non-coding RNAs are miRNA. As illustrated in the examples the method provide specific in situ detection by non-radioactive labeled LNA probes for miRNA even in standard formalin-fixed and paraffin-embedded (FFPE) tissue sections and in particular Example 5 show that the present method yield results that are superior to those obtained with an ISH hybridization mix that comprise formamide.

Although an irritant, guanidinium is not mentioned in the EU Dangerous Substances Directive (67/548/EEC) and guanidine hydrochloride is used in the treatment of the neuromuscular condition called Lambert-Eaton myasthenic syndrome at dosages up to 40 mg/kg/day (U.S. Pat. No. 7,521, 479) indicating that guanidinium is relatively non-toxic to humans. However, whereas example 6 show that salts of guanidinium or guanidine may substitute formamide in the method, the preferred embodiment of the method is one wherein the chaotropic component in the ISH hybridization mix is urea.

Urea is in general considered non-toxic. Urea is widely used as an active component in various skin-treatment products, and when used as a diuretic it may be given in dosages of about 1 to 2 g/kg/day, even when injected or infused (U.S. Pat. No. 7,521,479).

Furthermore the examples illustrate a method wherein the chaotropic component in the ISH hybridization mix is urea appears superior to one wherein the chaotropic component is guanidine hydrochloride (Example 6).

The small size (approx 22 nts) and often low level of expression of different miRNAs require use of sensitive probes for their detection by ISH. As described in WO 06/069584 LNA probes are particularly suitable to serve for this purpose as the use of LNA results in probes with improved sensitivity and high sequence specificity especially for small RNA target sequences. Accordingly in a preferred embodiment the situ hybridization probe contains one or more LNA monomers. LNA comprising in situ hybridization probes wherein the hybridization probe is labeled in both 3' and 5'end with digoxigenin (DIG) are particularly preferred. As shown in the examples excellent results were obtained with relatively short LNA-probes, comprising approximately 30% LNA monomers.

In general the method is not depending on the labeling of the hybridization probe, The probe may as well be labeled with streptavidin, biotin or a compound for which specific antibodies are available which include: fluorescein; dinitrophenol; amphetamine; barbiturate; acetaminophen; acetohexamide; desipramine; lidocaine; chloroquinine; quinine; ritalin; phenobarbital; phenytoin; fentanyl; phencyclidine; methamphetamine; metaniphrine; digoxin; penicillin; tetrahydrocannibinol; tobramycin; nitrazepam; morphine; Texas Red; TRITC; primaquine; progesterone; bendazac; carbamazepine; estradiol; theophylline; methadone; methotrexate; aldosterone; norethisterone; salicylate; warfarin; cortisol; testosterone; nortrptyline; propanolol, estrone; androstenedione, biotin, thyroxine, and triiodothyronine, biotin or digoxigenin. Also radioactive labeled, or metal- (gold-labelled) probes are contemplated.

In one particularly preferred embodiment the method comprise a step of hybridization wherein the cellular specimen is contacted with a hybridization-solution comprising:
  at least one non-radioactive labelled probe comprising 7-22 nucleotides which are capable of hybridizing to a specific RNA sequence.
  a hybrid stabilizing agent selected form the group of salts of mono- and di-valent cations. Preferred salts are sodium citrate or sodium chloride optionally further buffered eg. with phosphate. In a preferred embodiment the hybrid stabilizing and buffering agent is SSC (SSC, 1×=0.15M sodium chloride and 0.015M sodium citrate). SSC is preferably used at a concentration of 1 to 8×, such as between 1.5 and 5×, 2 and 4× or 2 and 3×. 2.5×SSC is preferred for in situ hybridization to miRNA targets when using the LNA-probes disclosed herein.
  urea in a concentration between 0.5 and 5 M; as illustrated in example 3 we obtained excellent results over the whole range between 0.5 and 4 M such as between 1 and 3M. The best signal-to-noise ratio was obtained with 2M urea. Importantly example 3 show that the chaotropic component is indispensable, no specific signal was obtained in the absence of urea.

Optionally the hybridization-solution in addition comprise:
  Denhardt's Solution at a concentration between 0-2× (preferably 1×); and
  from 0-0.5 mg/ml of a carrier RNA. The preferrer carrier RNA is yeast t-RNA at a final concentration of approximately 0.25 mg/mL.

Depending on the particular target/probe combination, the concentration of hybrid stabilizing and buffering agent and the type and concentration of chaotropic agent the optimal hybridization temperature vary considerable. In general the hybridization temperature is between 35° C. and 65° C. and the samples hybridize for 5 min to over night, such as for 5 to 240 min, 30 to 120 min or 5 to 60 min even 30 to 60 min. A number of formulas are available for arriving at an approximate hybridization temperature. The nearest-neighbor model, (SantaLucia, J, Jr. Proc. Natl. Acad. Sci. USA 1998, 95: 1460-5) is a preferred model. It should be noted that LNA-enhanced oligonucleotides have different melting properties from DNA oligonucleotides. It is advisable to use the oligo Tm predicting tool at http://www.exiqon.com/ls/homeoflna/Oliqo-tools/tm-prediction-tool.htm. This tool is based on a modified nearest-neighbor thermodynamical model and on over 10,000 LNA oligonucleotide measurements, and provide reliable estimates. However as illustrated in example 4 even small differences in the hybridization temperature produce significant differences. Consequently the present method imply an experiment to establish the optimal hybridization temperature for a specific combination of specimen, probe and target.

A detailed description of the method is disclosed in example 1.

Whereas the method is developed for FFPE it is construed that any type of cellular specimens that are fixed by use of cross-linking fixatives can be used with the method. thought freeze sections. Due to its remarkable robustness we believe the method only require small adjustments to perform well on specimens fixed using denaturating fixatives such as alcohol and/or acetone, or even by cryopreservation.

As illustrated in Example 2 the method enables specific analysis of individual pre-miRNA and mature miRNA. The specific detection of the double stranded pre-miRNA show that the method can be used to detect a wide range of small RNAs including small double-stranded RNAs such as siRNAs which are double-stranded RNAs wherein the complementary strands are about 22 nt long each. We envision that the method even is applicable for detection of mRNA.

As illustrated in the examples the method is particularly robust and reliable. Such a robust and reliable method is a prerequisite for meaningful quantification. As illustrated in example 7, 8 and 9. The method can be used to obtain semi-quantitative expression data.

Accordingly, in a further embodiment the method comprise a step wherein the hybridization signal is visualized by formation of the dark-blue NBT-formazan precipitate, and further comprise a quantization comprising the steps of:
  taking a number, such as 8-17, random images from within the tumor area,
  checking that said random images contain evident cancer cells, excluding those images which do not, also excluding images with tissue and staining artifacts,
  employing a supervised segmentation based on Bayesian classification trained to recognize blue pixels (i.e. NBT-formazan precipitate),
  quantify the relative miR-21 level by estimating either the total blue area (TB=B+P) and use TB as a measurement of the specific RNA level in the sample.

In general it is advantageous to counterstained specimens with vary histochemical stains to improve the contrast and facilitate the recognition of cellular components. Hematoxylin is a frequently used basic dye that stains nuclei blue due to an affinity to nucleic acids in the cell nucleolus. More histochemical stains may be combined to even further improve the analysis of the specimen. Hematoxilin is for instance often combined with eosin, an acidic dye that stains the cytoplasm pink.

Most of the specimens in the example was stained with nuclear fast red which stain cell nuclei bright red.

Specimens are counterstained with nuclear fast red (see example 7, 8 and 9) are very suitable for the semi-quantitative analysis and allow the calculation of another estimator to supplement the total blue area relative to nuclear red stained area (TBR) estimator. The steps to arrive at this estimator is based on specimens wherein the hybridization signal is visualized by formation of the dark-blue NBT-formazan precipitate and the specimens also are counterstained with nuclear fast red, and further comprise a quantization comprising the steps of:
  taking a number, between 8-17, random images from within the tumor area,
  checking that said random images contain evident cancer cells, excluding those images which do not, also excluding images with tissue and staining artifacts,
  employing a supervised segmentation based on Bayesian classification trained to recognize blue pixels (i.e. NBT-formazan precipitate), red pixels (i.e. nuclear fast red) and purple pixels (i.e. pixels colored with both NBT-formazan and nuclear fast red) to estimate the blue areas (B) and the red areas (R) and the purple areas (P)
  quantify the relative level of the RNA by estimating either the total blue area (TB=B+P) and/or the relative total blue area (TBR=TB/TR, wherein total red area TR=R+P) and use TB and/or TBR as a measurement of the specific RNA level in the sample.

The method is preferably used to quantify the level of small, non-coding RNA, in particular miRNAs.

The crucial component of the present invention is the improved, formamide-free, hybridization buffer that is especially suitable for detecting of small non-coding RNAs in standard formalin-fixed and paraffin-embedded (FFPE) tissue sections with LNA-probes by in situ hybridization, the buffer comprise 0.5 to 5 M of a chaotropic component selected from the group comprised of urea and salts of guanidinium (or guanidine) or a mixture of two or more members of the group.

In one embodiment the hybridization buffer comprise a chaotropic component or the mixture of chaotropic components that are selected from the group of urea and guanidine hydrochloride. However, urea is the preferred chaotropic component as it is considered non-toxic in the amounts it is being used in the present context. Example 5 show that this buffer results that are superior to those obtained with an ISH hybridization mix that comprise formamide, furthermore the urea-based buffer is stable for at least 13 months at 4° C. This is in stark contrast to ISH-buffers based on formamide, which we have observed have a short shelf-life at 4° C.

The hybridization buffer of the invention typically further comprise:
  a hybrid stabilizing agent selected form the group of salts of mono- and di-valent cations. The hybrid stabilizing agent may be a buffer in itself, or it may be further buffered e.g. with phosphate buffer,
  urea in a concentration between 0.5 and 5 M;
  Denhardt's Solution in an amount of 0-2×; and
  a carrier RNA, such as yeast t-RNA, in an amount of 0-0.5 mg/ml.

Numerous publications indicate that LNA-probes are especially well suited for the ISH of miRNA, see e.g. Wienholds et al. (2005) Science 309, 310-311. Accordingly one aspect of the invention is a kit for detection of at least one small non-coding RNAs in standard formalin-fixed and paraffin-embedded (FFPE) tissue by in situ hybridization, said kit comprise the improved, formamide-free, hybridization buffer of any claims 10 to 13 and least one LNA-probe optimized for the specific detection of said one small non-coding RNA. Preferably the kit is directed to the detection of a microRNA, and the at least one enclosed LNA-probe is preferably labeled both in its 3' and 5'-end with digoxigenin.

miRs represent robust and stable biomarkers in formalin fixed paraffin embedded FFPE material. There are several publications demonstrating that miRs are stable and regulated in cancer. A recent paper by Schetter et al (JAMA, 2008) describes the use of miR as prognostic biomarkers in colon cancer. Of particular interest is that the authors were able to separate non-cancerous specimens from cancerous specimens by the use of one miR (miR-21). This separation was supported by multivariate analyses, showing that miR-21 expression was independent of disease stage. It is evident from literature as well as from example 1, 2, 5, 7, 8 and 9 that in general the miR-21 predominantly is expressed in fibroblast-like cells located in the stromal compartment of the tumors whereas the cancer cell compartment generally expresses very low levels of miR-21. However, recently we (Nielsen et al. (2011) Clin Exp Metastasis 28: 27-38) have shown that in certain tumors there are clusters of cancer cells that express high levels of miR-21. Such significant spatial distribution immediately signified to the inventors that data obtained from a semi-quantitative miR-21 ISH, such as the one described herein, would be especially useful as a diagnostic tool. The use of the semi-quantitative miR-21 ISH as a diagnostic tool is illustrated in example 9. In brief the method of example 9 is a method of predicting the disease-free survival of a stage II colon cancer patient comprising:

a) determining the relative level of miR-21 in at least one representative tissue section from a stage II colon cancer of said patient determined by the method of claim 7 and, b) comparing the level of miR-21 in the patient to a set of relative levels of miR-21 obtained by the method of claim 7 from a reference panel of stage II colon cancer samples obtained from a reference panel of patients with known disease history, c) grouping the reference panel in tertiles according to the relative level of miR-21 determined by the method of claim 7; and d) taking a miR-21 level of said at least one representative tissue section from a stage II colon tumor from said patient that falls within the miR-21 level of the upper (high expressing) tertile as indicative of an increased likelihood of short disease-free survival, and taking a miR-21 level of said at least one representative tissue section from a stage II colon tumor from said patient that falls within the miR-21 level of the lower (low expressing) tertile as indicative of an increased likelihood of long disease-free survival.

According to literature (e.g. Bartels (2009) Clin Chem 55, 623-631), a wide range of miRs can be used as prognostic and diagnostic markers of various types of cancer. The inventors stipulate that in those instances where the miRs express a significant spatial distribution the semi-quantitative ISH of the present invention will prove to be a valuable addendum to the diagnostic tool box.

The invention is further illustrated in the following non-limiting examples and the figures wherein FIG. 1. Shows the result of miRNA in situ hybridization using the non-toxic, chaotropic compound urea in the prehybridization and hybridization buffers. On the figure are eight panels: a-d in color and a'-d' in b/w, showing miR-21, scrambled, miR-21+unlabeled and U6 snRNA. Black arrow points at examples of specific signals.

Figure 2:
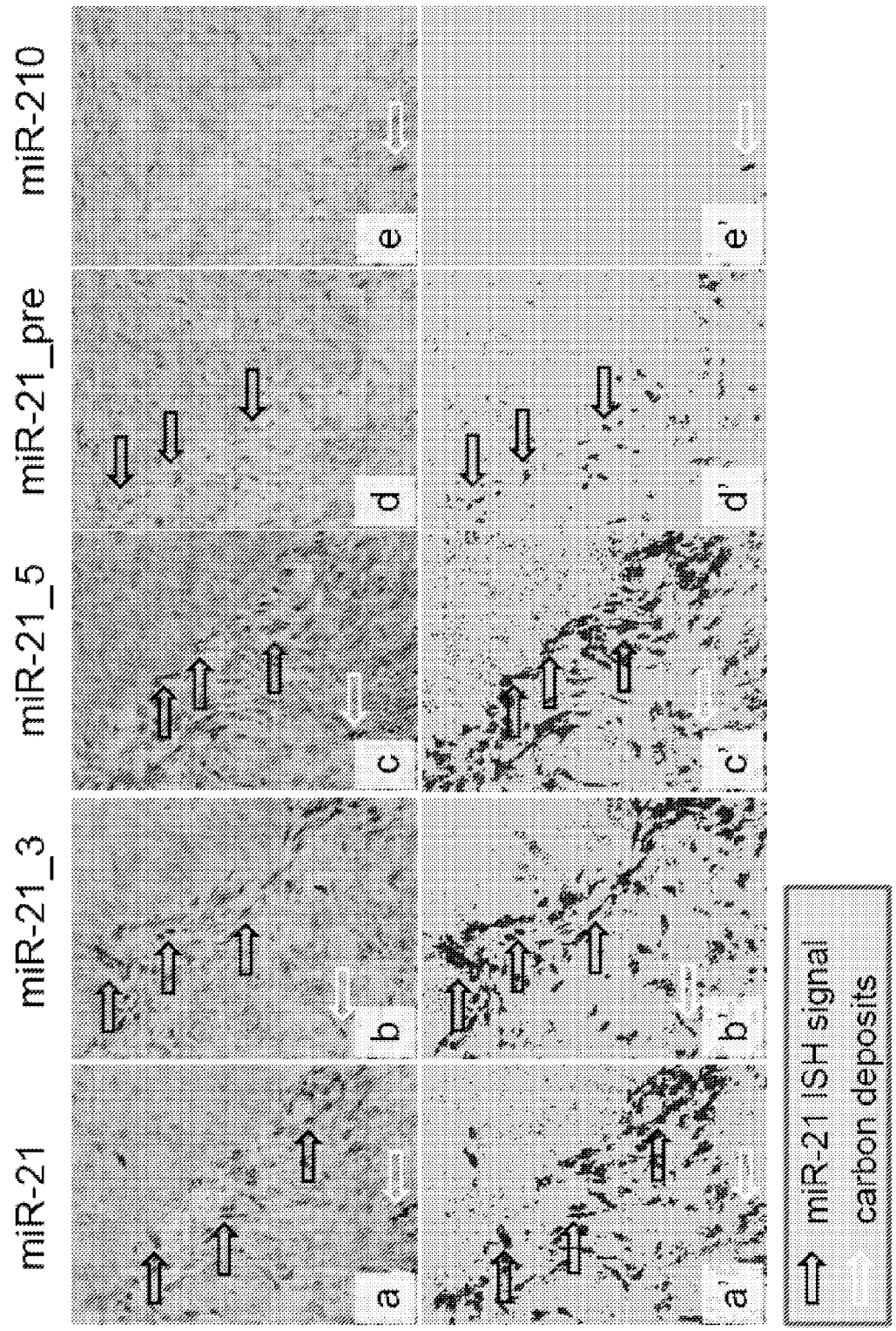

FIG. 2. Shows the specificity of the method. Four variants of miRNA-21 probes was analysed by in situ hybridization using 2 M urea in the hybridization buffer. Ten panels: a-e in color and a'-e' in b/w, showing the ISH using the miR-21, the miR-21__3, the miR-21__5, the miR-21_pre and the miR-210. Black arrow points at specific signals, white arrow at carbon deposits.

Figure 3:
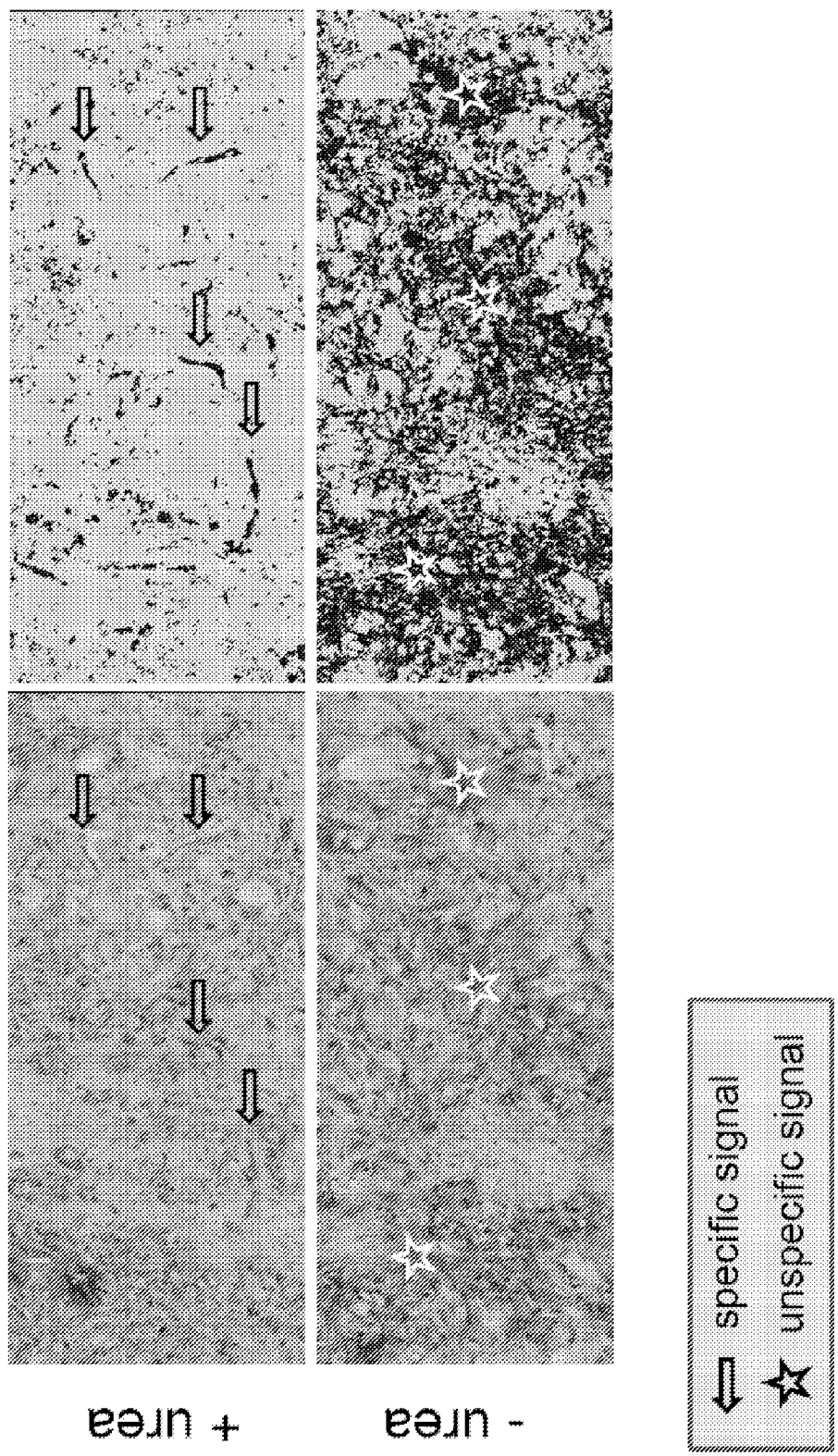

FIG. 3. Shows results of miRNA-126 ISH detection in response to zero and 2 M of urea in the pre-hybridization and hybridization buffers. Shown in the figure are Four panels: two in color, two in b/w, showing miR-126 detection in the presence/absence of urea. Arrow points at specific signals, star at unspecific signals.

Figure 4:
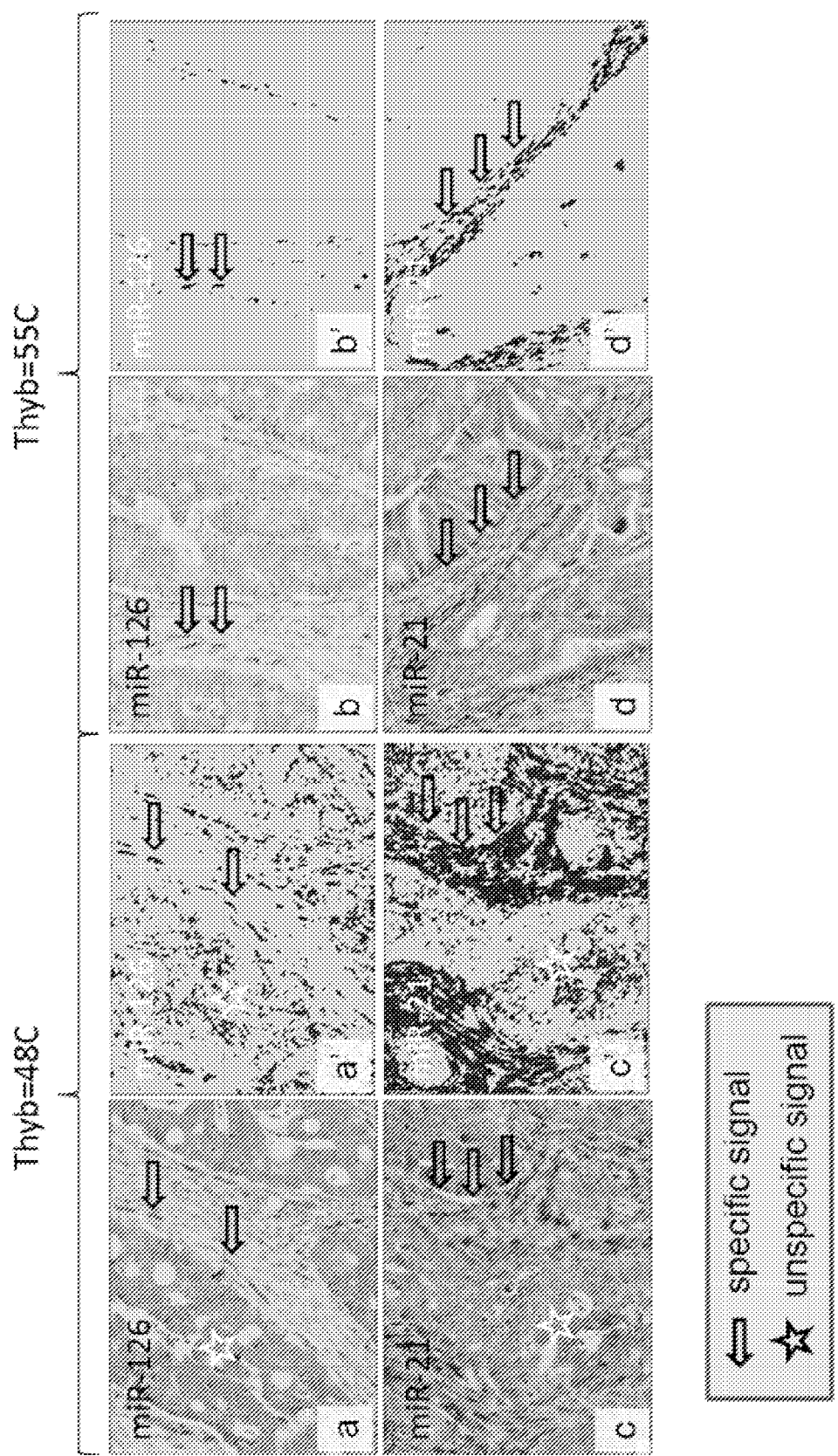

FIG. 4. Shows miRNA-21 (Panels c-d) and miRNA-126 (Panels a-b) in situ hybridization at 48° C. and 55° C. in the presence of 2 M urea in the hybridization buffer. Panels: a-d are in color and a'-d' in b/w. Temperature of hybridization is abbreviated Thyb. Arrow points at specific signals, star at unspecific signals.

Figure 5:
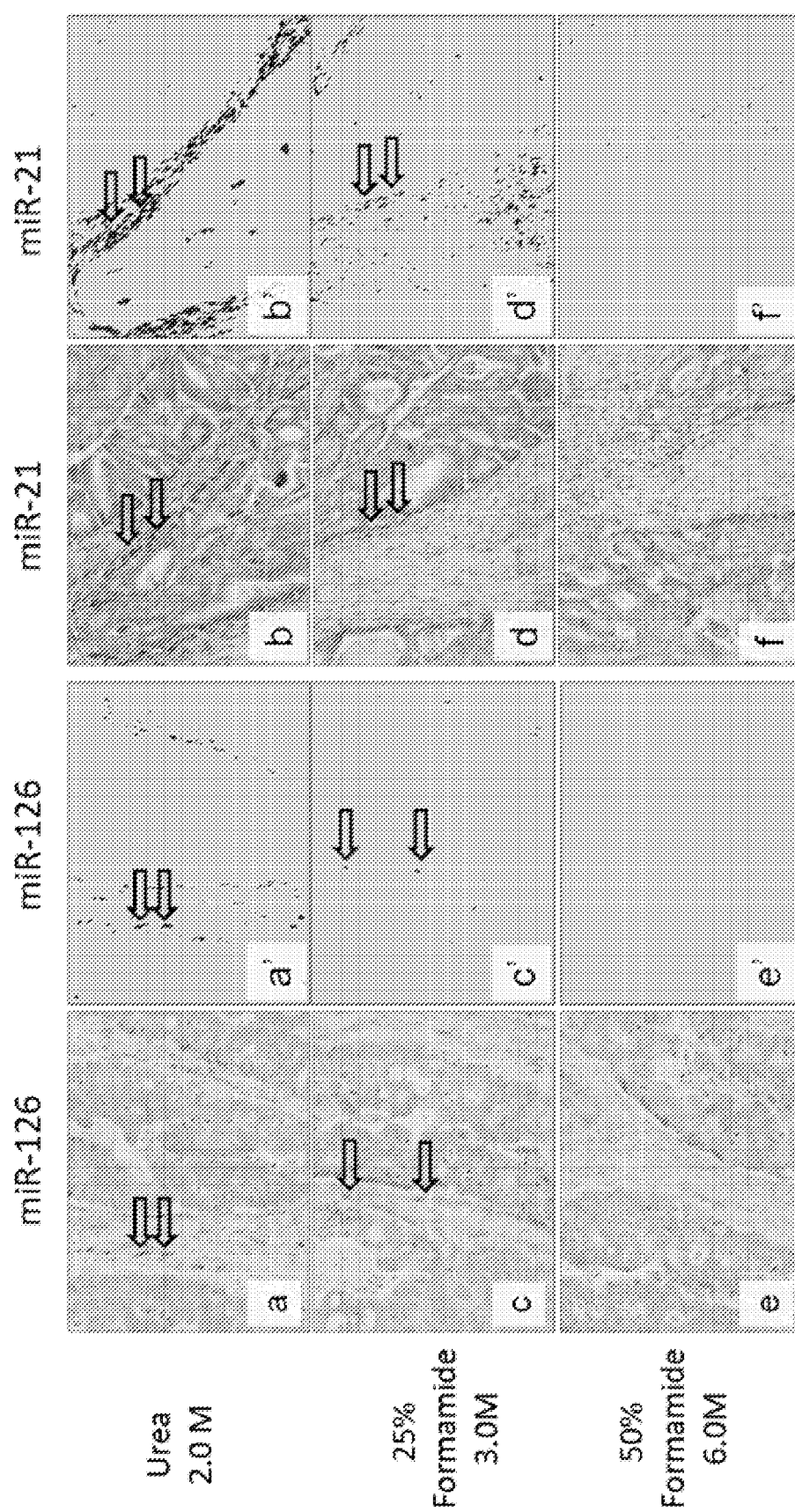

FIG. 5 Shows miRNA-21 (Panels b,d,f) and miRNA-126 (Panels a,c,e) in situ hybridization at 55° C. in the presence of either 2 M urea, 3 M formamide or 6 M formamide in the prehybridization and hybridization buffers. Panels: a-f are in color whereas a'-f' are in b/w. The arrow points at examples of specific signal.

Figure 6:
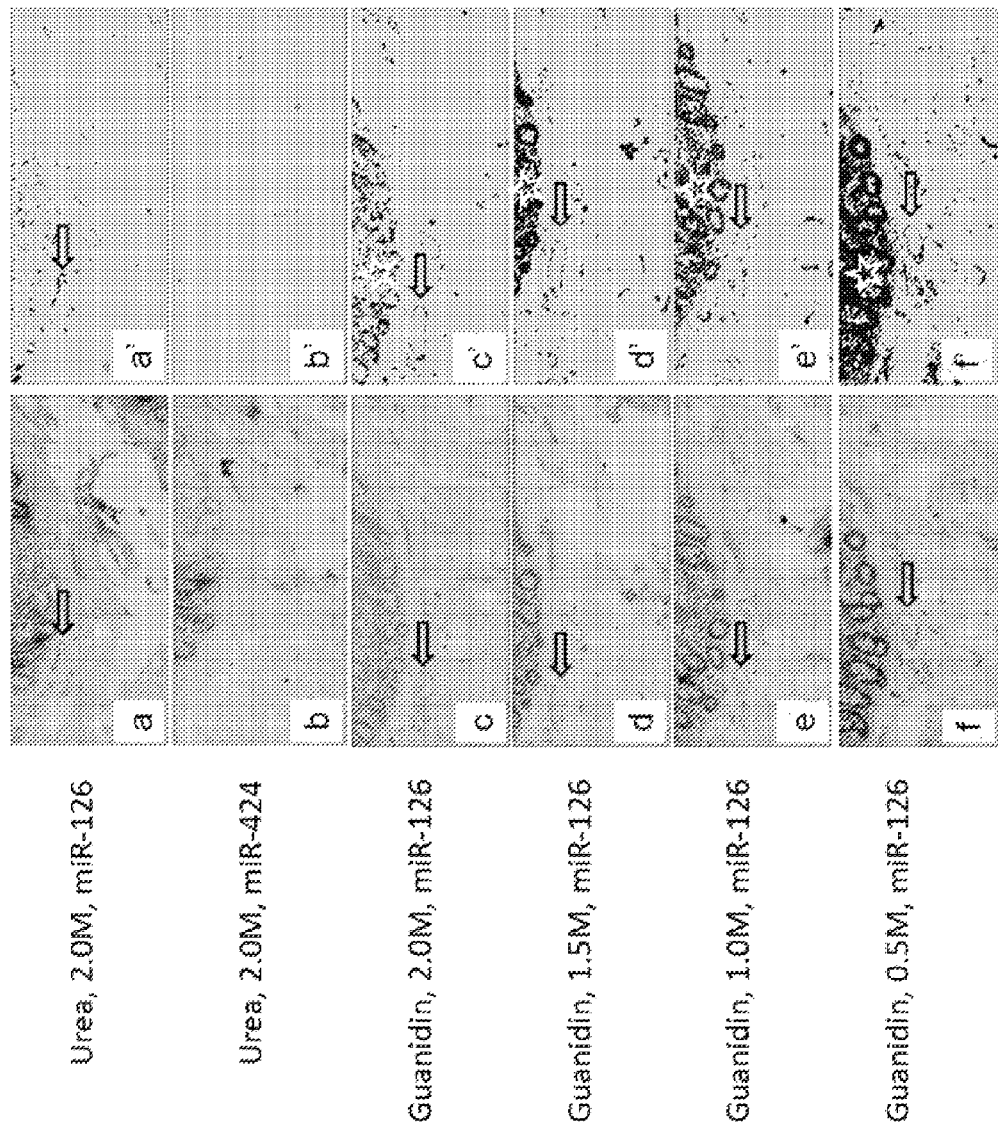

FIG. 6 shows the results of miRNA-126 detection in colon tissue by in situ hybridization at 55° C. in the presence of 2 M urea (Panel a) and various concentrations of guanidine in the pre-hybridization and hybridization buffers (Panels c-f). Panel a-f in color and a'-f' in b/w. Arrows point at vessels, star indicate epithelium.

Figure 7:
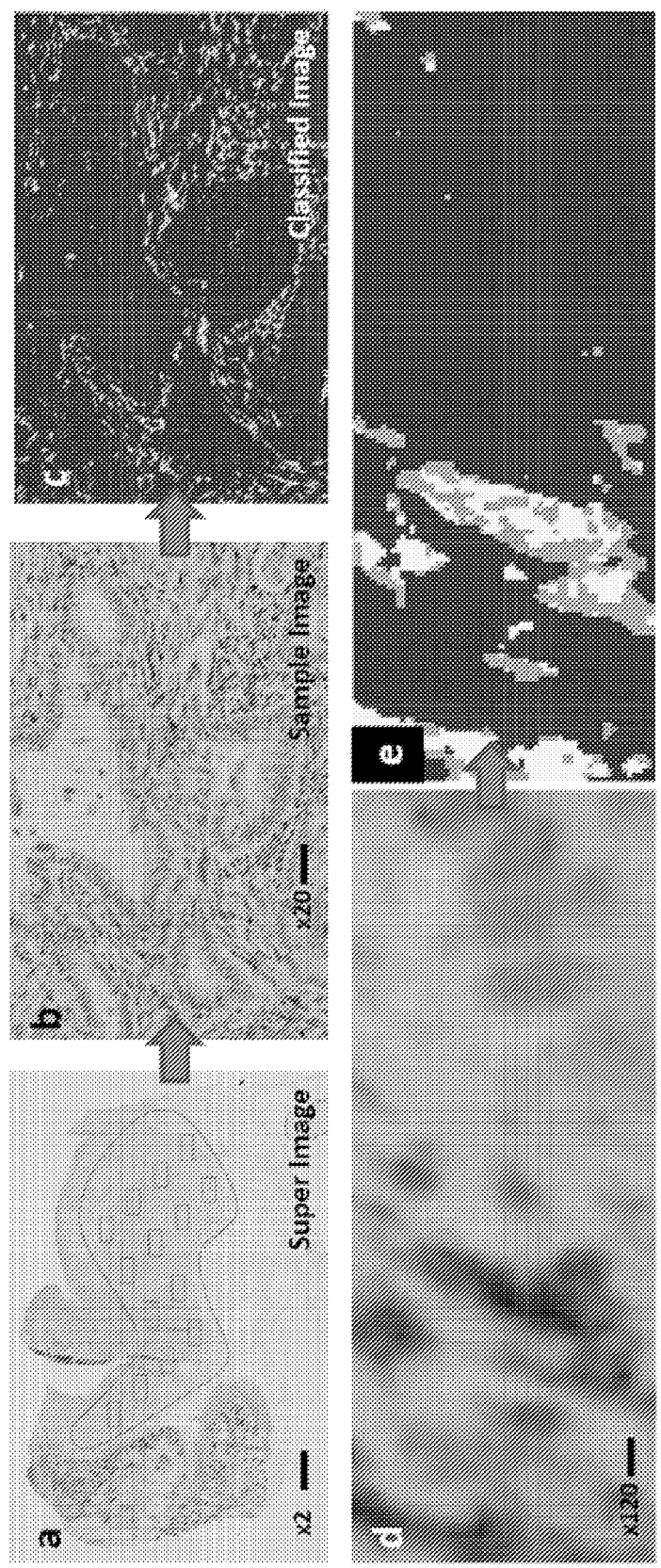

FIG. 7. Illustrate the semi-quantitative ISH exemplified by the image sampling and image analysis of a miR-21 in situ hybridization signal in colon cancer. Panel (a) present a typical example of a whole tissue section (panel a) with normal mucosa, tumor area and submucosa after in situ hybridization for miR-21 and counterstaining with nuclear red. The tumor area is encircled and random systematically placed image positions are indicated by squared frames. Sample images are captured with a 20× objective at the systematically placed image positions. Panel (b) show one such sample image. The sample images are subsequently processed with a supervised pixel classifier which have been trained to separate the blue in situ hybridization signal from the red counter stain and the purple in situ hybridization signal overlaying the nuclear red, panel (c). Note false color red correlate to nuclear fast red in panel (b) whereas the blue ISH signal in panel (b) is shown as a green false color in panel (c). The area within the frames indicated in the lower left corner of panel (b) and (c) are in enlarged and shown in panel (d) and panel (e). Note the blue in situ hybridization signal of panel (d) appear as bright green, the purple signal of panel (d) is as yellow and the red signal of panel (d) appar as bright red in the classified image, panel (e). Bars in panel (a): 250 µm, in panel (b) and (c): 40 µm, and in panel (d) and (e): 4 µm.

Figure 8A:
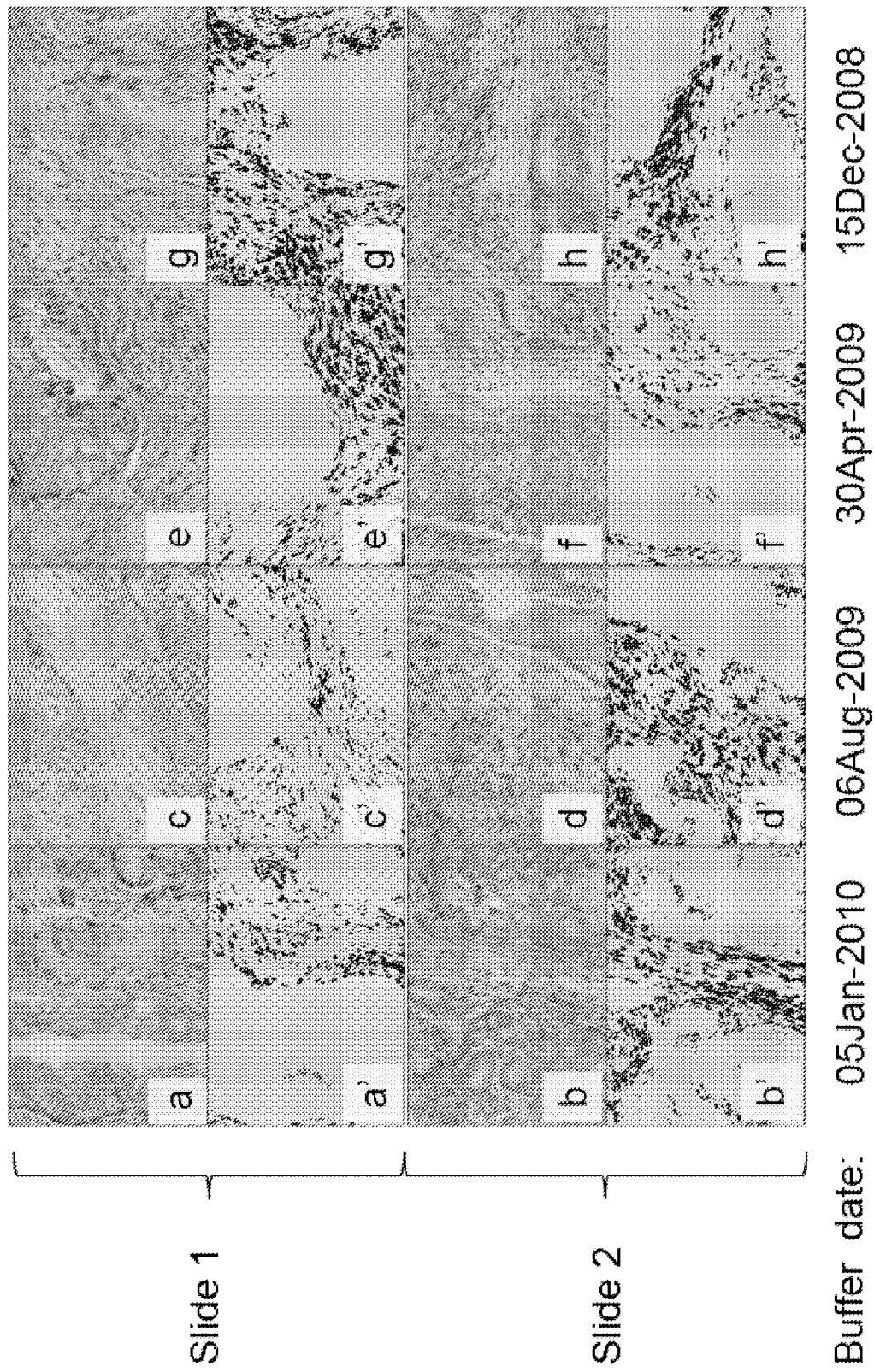

FIG. 8A. Illustrate the stability of the hybridization buffer by an miRNA-21 in situ hybridization on colon cancer tissue hybridized with an urea-containing hybridization buffer prepared according to the date indicated in figure. Panel (a)-(h) are color, (a')-(h') are b/w.

Figure 8B:
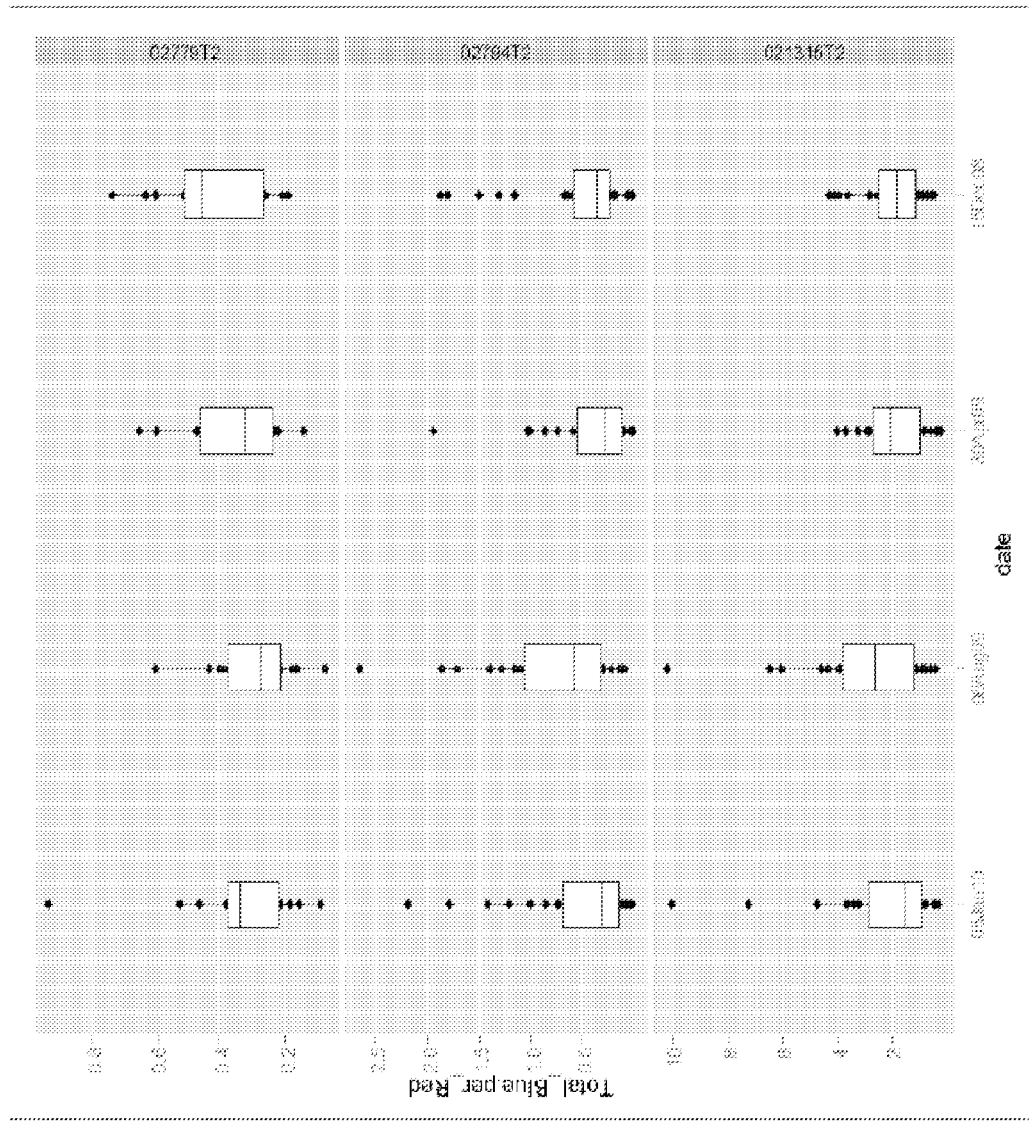

FIG. 8B. Is a presentation of the semi-quantitative data obtained by a number of miRNA-21 in situ hybridization on colon cancer tissue hybridized with an urea-containing hybridization buffer prepared according to the date indicated in figure. Boxes indicate the distribution of expression values from the $25^{th}$ to the $50^{th}$ percentile. The dots indicate observations outside the $25^{th}$ to the $50^{th}$ percentile. The horizontal line in the box is the median.

Figure 9:
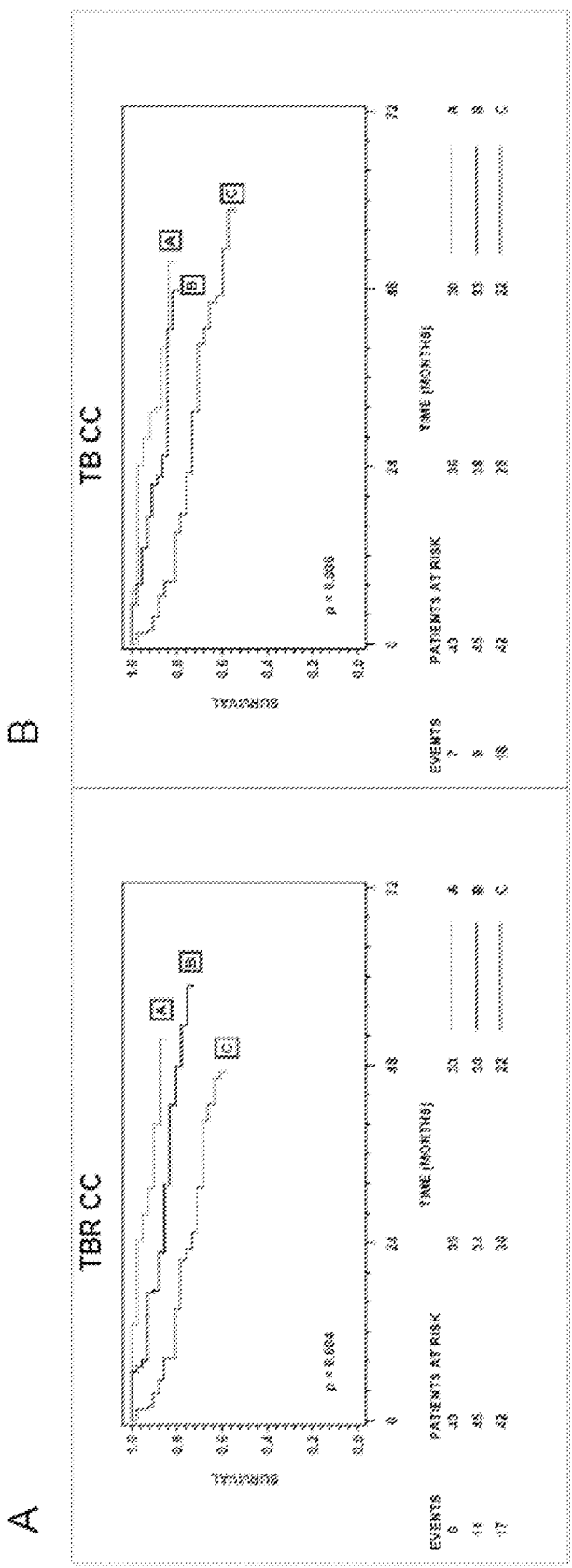

FIG. 9 shows a tertile plot of Kaplan-Meier estimates of miRNA-21 in situ hybridization signal. Cox regression analyses were performed to compare the statistical power of the observed miRNA-21 expression levels, measured as TBR values in 130 colon cancer patients (panel A) and TB values in the same 130 colon cancer patients (panel B).

[A] indicate the lower tertile (the 33.3% of patients with the lowest miR-21 level as estimated with the method of the invention).

[B] the intermediate tertile.

[C] indicate the highest tertile (the 33.3% of patients with the highest miR-21 level as estimated with the method of the invention).

Figure 10:
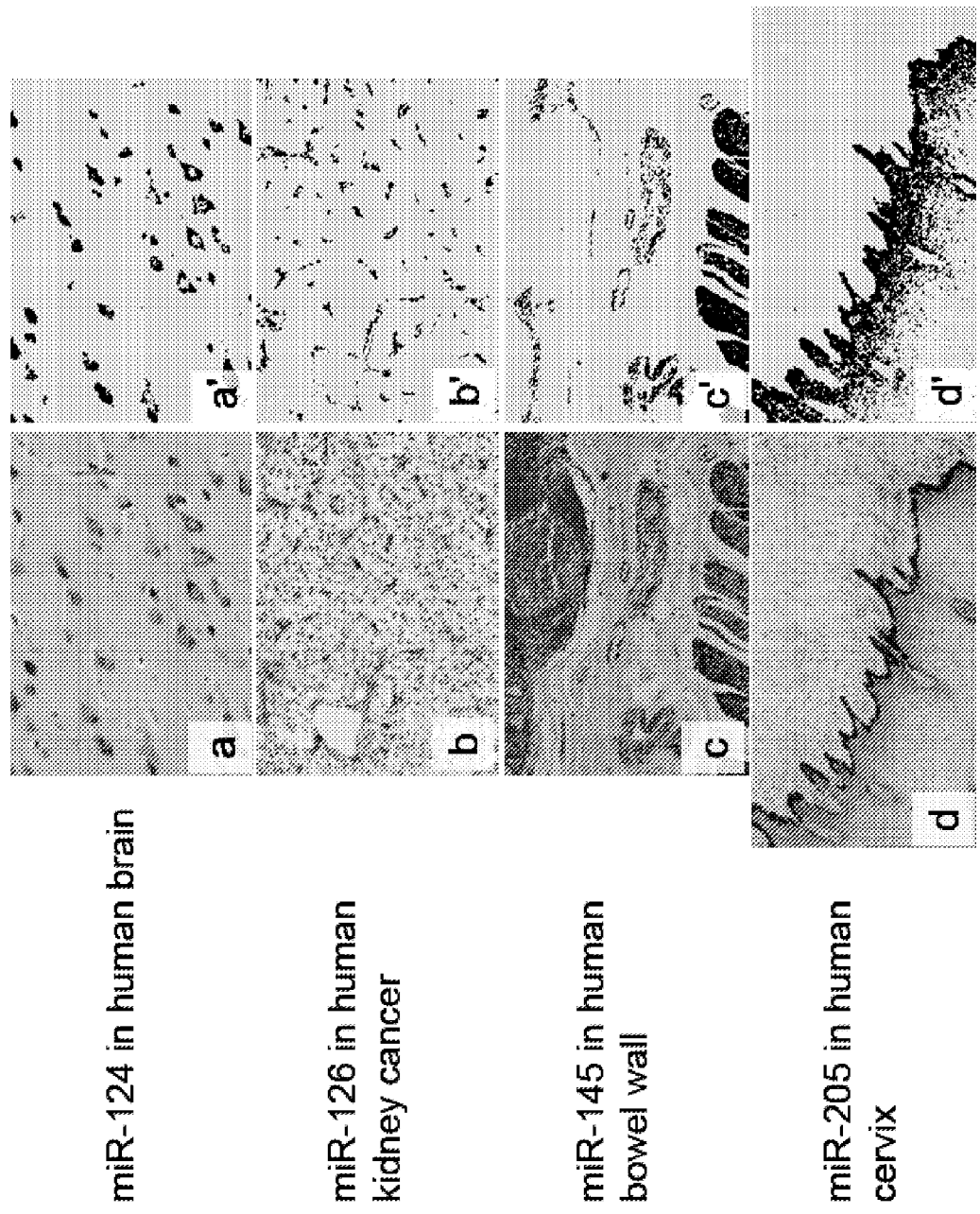

Indicated are the number of events=deaths in the three tertiles during the 72 months of observation and the number of patients in each group at 0, 24 and 48 months FIG. 10 shows the results of in situ hybridization of four miRNA species in different types of human tissue using 2 M urea in the hybridization buffer. The four probes targeting miRNA-124 in brain (upper panel), miRNA-126 in kidney, miRNA-145 in the bowel wall (Panel c) and miRNA-205 in cervix (lower panel). The 4 panels to the left (a-d) are color, the 4 panels to the right (a'-d') are b/w.

Figure 11:
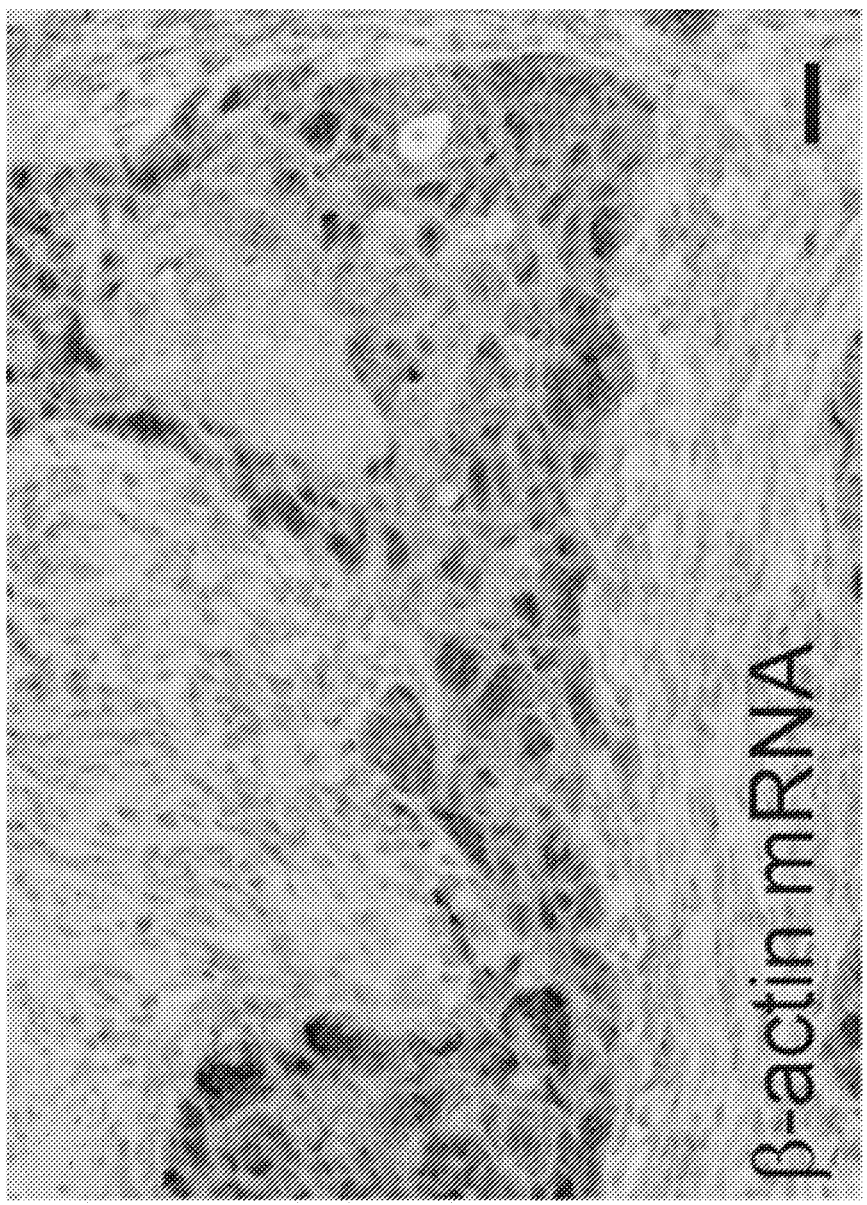

FIG. 11 shows the results of in situ hybridization of human β-actin mRNA in a human esophagus cancer using an LNA probe. The FFPE sample were purchased from Proteogenex (Culver City, Calif.). Bar 40 μm.

EXAMPLES

General Methods

Tissue Sources.

Table 1 identifies the providers of the routinely-fixed, paraffin-embedded specimens used in Examples 1-10 for miRNA in situ hybridization analyses.

TABLE 1

Providers of the FFPE specimens used in Examples 1-10. Ranx05 is a reference to theDanish RanX05 Colorectal Cancer Study. Some results from studies of this patient-cohort has been published in *Scand. J. Gastroenterol.*, February 2000; 35(2):212-7.

| Example and panel | Tissue type | Tissue providers |
|---|---|---|
| 1a-d | Colon cancer | Hvidovre Hospital, Ranx05 |
| 2a-e | Lung cancer | Proteogenex |
| 3a-b | Colon cancer | Proteogenex |
| 4a-d | Colon cancer | Proteogenex |
| 5a-f | Colon cancer | Proteogenex |
| 6a-f | Normal colon | Proteogenex |
| 7a | Colon cancer | Hvidovre Hospital, Ranx05 |
| 7b | Colon cancer | Hvidovre Hospital, Ranx05 |
| 7c | Colon cancer | Hvidovre Hospital, Ranx05 |
| 7d | Colon cancer | Hvidovre Hospital, Ranx05 |
| 7e | Colon cancer | Hvidovre Hospital, Ranx05 |
| 8A(a-h) | Colon cancer | Proteogenex |
| 8B | Colon cancer | Proteogenex |
| 9 | Colon cancer | Hvidovre Hospital, Ranx05 |
| 10a | Normal brain | Odense University Hospital (BW Christensen) |
| 10b | Kidney cancer | Proteogenex |
| 10c | Normal colon | Proteogenex |
| 10d | Normal cervix/cancer | Proteogenex |

Nucleotide Sequences.

Table 2 provides an overview of the miRNA species discussed in Examples 1-10 and the sequences of the corresponding, LNA-enhanced oligonucleotides used as probes. Information on LNA content and predicted melting temperatures (Tm) against a complementary RNA sequence in a medium salt buffer (10 mM sodium phosphate, 100 mM NaCl, 0.1 mM EDTA, pH 7.0) is also offered. All probes were designed by Exiqon, Denmark.

TABLE 2

Overview of the miRNA species and probes (Exiqon, Denmark) used in Examples 1-10.

| Seq ID NO | miRNA species | Probe | Sequence | LNA content (%) | Predicted $T_m$ |
|---|---|---|---|---|---|
| 1 | hsa-miR-21 | miR21 | tcaacatcagtctgataagcta | 32 | 82.7 |
| 2 | hsa-miR-21 | miR21_3 | tcaacatcagtctga | 40 | 80.6 |
| 3 | hsa-miR-21 | miR21_5 | acatcagtctgataagc | 41 | 81.7 |
| 4 | hsa-miR-21 | miR21_loop | catgagatttcaacagtca | 42 | 82.4 |
| 5 | hsa-miR-124 | miR124 | ggcattcaccgcgtgcctta | 25 | 89.8 |
| 6 | hsa-miR-126 | miR126 | gcattattactcacggtacga | 33 | 84.5 |
| 7 | hsa-miR-145 | miR145 | agggattcctgggaaaactggac | 30 | 84.3 |
| 8 | hsa-miR-205 | miR205 | agactccggtggaatgaagga | 29 | 87.3 |
| 9 | hsa-miR-210 | miR210 | gctgtcacacgcaca | 27 | 79.7 |
| 10 | hsa-miR-424 | miR424 | ttcaaaacatgaattgctgctg | 41 | 83.3 |
| 11 | no miRNA | Scrambled | gtgtaacacgtctatacgccca | 32 | 87.3 |
| 12 | no miRNA | U6 snRNA | cacgaatttgcgtgtcatcctt | 27 | — |

Detection Systems and Image Analysis.

Visiopharm's integrated microscope and software module (Visiopharm, Hoershoelm, Denmark), comprising a Leica DM 6000B microscope (Leica, Wetzlar, Germany) equipped with an automated stage and slide loader (Ludt, Hawtorne, USA) and a DP72 CCD camera (Olympus, Tokyo, Japan), was used for image analysis. Exposure of sample images was kept at 6.993 milli-seconds with red-green-blue (RGB) values at 170-180 in blank areas. Supervised segmentation based on Bayesian classification, where each pixel is classified according to its chromatic properties, was done using the Visiomorph (Visiopharm, Hoershoelm, Denmark) software tool. The following colors were identified for supervised classification: Blue=in situ hybridization signal. Purple=in situ hybridization signal overlaying nuclear red. Red=nuclear red stain separated from unstained background.

Presentation of Data.

The figures in the Results Sections of Examples 1-10 consist of a number of colore images (primary data) and corresponding gray-scale images. The gray-scale images is a representation of the primary color images and supposed to visualize the in situ hybridization signal in a form that reproduce well during the printing process typically used for patent documents. Most grayscale images are recognized by letters followed by an apostrophe. These grayscale images were obtained using a trained pixel classifier where the color images are translated into black and white images. This way, blue and purple hybridization signals were translated into black, whereas red and background signals were translated into light gray or white colors. References in the Results Sections of Examples 1-10 are to the colored images only. Table 3 provides an overview of the magnifications and type of images used, as well as the size (in μm) of the tissues depicted by the figures in the Results Sections of Examples 1-10.

TABLE 3

Information on the images in the Results Sections of Examples 1-10.

| Example | Lens | Image | X, μm | Y, μm |
|---|---|---|---|---|
| 1a-d | x20 | Standard | 620 | 460 |
| 2a-e | x40 | Standard | 230 | 310 |
| 3a-b | x20 | Stitched | 1070 | 480 |
| 4a-d | x20 | Standard | 620 | 460 |
| 5a-f | x20 | Standard | 620 | 460 |
| 6a-f | x20 | Stitched | 1200 | 500 |
| 7a | x1.25 | Stitched | 24000 | 13000 |
| 7b | x20 | Cropped | 620 | 400 |
| 7c | x20 | Cropped | 620 | 400 |
| 7d | x20 | Zoom | 75 | 26 |
| 7e | x20 | Zoom | 75 | 26 |
| 8A(a-h) | x20 | Standard | 620 | 460 |
| 8B | NA | NA | NA | NA |
| 9 | NA | NA | NA | NA |
| 10a | x40 | Standard | 310 | 230 |
| 10b | x20 | Standard | 620 | 460 |
| 10c | x20 | Stitched | 1470 | 1100 |
| 10d | x20 | Stitched | 970 | 540 |

Example 1

Non-Toxic In Situ Hybridization of miRNA in Routinely-Fixed, Paraffin-Embedded Specimen Using DIG-Labeled LNA Probes is Enabled by the Chaotropic Compound Urea Introduction Illustrated by miRNA-21 expression in routinely-fixed, paraffin-embedded specimen by in situ hybridization analysis, Example 1 shows that urea in the hybridization buffer facilitates a non-toxic hybridization of miRNA species.

Methods

An in situ hybridization protocol is described for the detection of miRNA-21 in routinely formalin-fixed and paraffin-embedded (FFPE) human colon cancer tissue specimens containing both normal mucosa and tumor tissue, were used (Table 1).

Probes.

LNA-containing oligonucleotides were designed by Exiqon, Denmark. For miRNA-21 detection, the LNA-enhanced sequence tcaacatcagtctgataagcta (estimated $T_m$=83° C.), digoxigenin-labeled at the 5'- and 3'-ends, was used at a concentration of 40 nM (Seq-ID No 1 in Table 2). An unlabeled version of the miR-21 probe with an identical LNA pattern was included in competition experiments. As positive control a 5' digoxigenin-labeled probe at 0.1 nM with the sequence: cacgaatttgcgtgtcatcctt and an estimated $T_m$ of 84° C., specific for U6 snRNA (Seq-ID No 12 in Table 2), was used. A 5'- and 3'-digoxigenin-labeled oligonucleotide with the scrambled sequence: gtgtaacacgtctatacgccca and an estimated $T_m$ of 87° C. (Seq-ID No 11 in Table 2) was included as negative control at 40 nM.

Water.

To prepare stock solutions, for dilutions and for washes, Milli-Q-grade, RNase depleted water was used.

Mounting Tissue Sections on Solid Support.

After trimming of the block, 6 μm thick sections of the FFPE specimens were cut and moved to a dry-sterilized Ziehl-Nielsen jar with 25° C. RNase-free water. The tissue sections were transferred to a water bath heated to 40-50° C., where they were stretched to avoid tissue folds, and then immediately mounted on SuperFrost®Plus slides (Microm International, Walldorf, Germany). The slides were air-dried 1-2 hours at 25° C. and stored at 4° C.

Deparaffination.

The paraffin sections on the SuperFrost®Plus slides were deparaffinized through 10 immersion baths containing xylene (baths 1-3), 99.9% ethanol (baths 4-6), 96% ethanol (baths 7-8) and 70% ethanol (baths 9-10). Baths 1, 2, 3, 6, 8, and 10 were 5-minute immersions, whereas baths 4, 5, 7, and 9 were 10-consecutive in-and-out immersions. The SuperFrost slides with the tissue sections were then placed in phosphate buffered saline (PBS) containing 137 mM NaCl, 2.7 mM KCl, 8 mM $Na_2HPO_4$ and 2 mM $KH_2PO_4$ (Cat. No. 70013-073, Invitrogen, Carlsbad, USA).

In Situ Hybridization Procedure with Non-Radioactive Chromogenic Detection.

The SuperFrost slides with the tissue sections were mounted in Tecan slide-covers and locked into Tecan flow-through cassettes, which were placed in a Tecan Freedom Evo automated hybridization instrument (Tecan, Mannedorf, Switzerland) and exposed to a continuous flow of the following buffers, enzymes, oligonucleotides and other components at the temperatures and for the time lengths indicated:

1) Wash: PBS at 25° C. for 6 min.
2) Wash: Protein Kinase K Reaction Buffer containing 5 mM Tris-HCl, 1 mM EDTA and 1 mM NaCl, pH 7.4, at 37° C. for 6 min.
3) Protein Kinase K treatment: Protein Kinase K Reaction Buffer containing 15 μg/ml Protein Kinase K (Cat. No. 03-115-887-001, Roche, Basel, Switzerland) at 37° C. for 8 min.
4) Wash: PBS at 25° C. for 6 min.
5) Prehybridization: Non-toxic, nuclease-free buffer containing 2.5×SSC (Cat. No. AM9765, Applied Biosystems/Ambion, Austin, USA); 2M urea; 1×Denhardt's Solution (Cat. No. 30915, Sigma-Aldrich, St. Louis, USA); and yeast t-RNA (Cat. No. 83853, Sigma-Aldrich, St. Louis, USA) at a final concentration of 0.25 mg/mL at 62° C. for 15 min.

6) Hybridization: same buffer as in Step 5), but also containing 40 nM miRNA-21 probe at 57° C. for 60 min.

7) wash: 5×SSC at 62° C. for 5 min.

8) wash: 1×SSC at 62° C. for 7 min.

9) wash: 0.2×SSC at 62° C. for 14 min.

10) wash: 0.2×SSC at 30° C. for 7 min.

11) Wash: PBS at 30° C. for 6 min.

12) Blocking of unspecific antibody binding: the DIG wash and Block Buffer Set (11-585-762-001, Roche, Switzerland) was used. The tissue sections were incubated in freshly prepared Blocking Solution (1:10 in maleic acid buffer: 0.1 M maleic acid, 0.15 M NaCl, pH 7.5) for 15 min at 30° C.

13) Detection of digoxigenin-labeled probes: alkaline phosphatase-conjugated sheep anti-digoxigenin (11-093-274-910, Roche, Switzerland) diluted 1:500 in Blocking Solution containing 0.1×PBS and 0.1% Tween-20.

14) Wash: PBS at 30° C. for 4 min.

15) Enzymatic development: nitra-blue tetrazolium (NBT/BCIP) ready-to-use tablets (Cat. No. 11-697-471-001, Roche, Switzerland) following the manufacturer's instructions, at 30° C. for 60 min.

16) Wash: KTBT buffer containing 50 mM Tris-HCl, 150 mM NaCl and 10 mM KCl at 30° C. for 10 min.

17) Wash: water at 25° C. for 2 min.

18) Counterstain: Nuclear Fast Red (Cat. No. H-3403, Vector Laboratories, Burlingame, USA) diluted 1:2 with water at 25° C. for 1 min.

19) Wash: water at 25° C. for 6 min.

Dehydration.

The SuperFrost slides with the tissue sections were dismantled from the Tecan chambers and flow-through cassettes and placed in tap-water. The slides were dehydrated through 6 ethanol baths: 70% ethanol (baths 1-2), 96% ethanol (baths 3-4), and 99.9% ethanol (baths 5-6). Baths 1, 3, and 5 were 10-consecutive in-and-out immersions, whereas baths 2, 4, and 6 were 5-minute immersions. Immediately following dehydration, the SuperFrost slides were then mounted with Eukitt medium (Cat. No. 361894-G, VWR, Herlev, Denmark).

Detection, Image Analysis and Presentation of Data.

Detection; image analysis and data presentation were done as described in the General Methods Section.

Results

FIG. 1 shows the results of miRNA in situ hybridization using the non-toxic, chaotropic compound urea in the prehybridization and hybridization buffers. A strong signal was obtained with the double-DIG-labeled miRNA-21 probe in parallel with little or no diffuse background stain (Panel a). The miRNA-21 signal is detected in the stromal compartment. No signal was observed with the double DIG-labeled scrambled probe (Panel b). Hybridization with a mixture of the miRNA-21 probe and unlabeled probe resulted in a strongly reduced ISH signal (Panel c). An ISH signal for snRNA U6 was observed in the nuclei of all cell types (Panel d). Data on magnification, tissue size and other information of relevance to the images, are offered in Table 3.

Conclusion

Based on the result obtained in Example 1, we conclude that in situ detection by DIG-labeled LNA probes for miRNA in FFPE is possible using the non-toxic, chaotropic compound urea in the hybridization buffer. And accordingly that the teratogenic formamide, which for decades was the chaotrope of choice in hybridization buffers for in situ hybridization, can be substituted by the non-toxic urea.

Example 2

Specific In Situ Hybridization of miRNA-21 by Variants of miRNA-21 Probes in Routinely-Fixed, Paraffin-Embedded Specimen by DIG-Labeled LNA in Urea-Based ISH Buffer Introduction Illustrated by in situ hybridization of variants of miRNA-21 probes including one covering the loop region of miRNA-21, Example 2 shows that ISH with the urea-comprising hybridization provide sufficient specificity to discriminate between individual pre-miRNA and mature miRNA species in routinely-fixed, paraffin-embedded specimens.

Methods

Mounting of tissue sections on solid support; deparaffination; the in situ hybridization procedure including the prehybridization step; and dehydration were done as described in the Methods Section of Example 1. Detection; image analysis; and data presentation were done as described in the General Methods Section.

Specimens.

Five serial tissue sections of human lung cancer tissue from a routinely-fixed, paraffin-embedded specimen identified in Table 1 were prepared as described in Example 1.

Probes.

Five double digoxigenin-labeled, LNA-enhanced oligonucleotides were designed by Exiqon, Denmark. Three probes including a full-length 22-mer (Seq-ID No 1 in Table 2), a 15-mer (Seq-ID No 2 in Table 2) and a 17-mer (Seq-ID No 3 in Table 2) all targeted to the stem-region of the pre-miRNA-21. A 19-mer (Seq-ID No 4 in Table 2) targeted the miRNA-21 loop region. The fifth probe, which targeted miRNA-210 (Seq-ID No 9 in Table 2), was used as negative control. All probes were tested at a final concentration of 40 nM.

Results

FIG. 2 shows the results of a specificity analysis of four variants of miRNA-21 probes by in situ hybridization using 2 M urea in the hybridization buffer. Analysis was done on serial tissue sections cut from the same FFPE specimen. The four probes targeting miRNA-21 all demonstrated an intense signal in the stromal fibroblast-like cells. For comparison, no in situ hybridization signal was obtained with the probe targeting miRNA-210. In addition to the miRNA-21 probe variants identified in the Methods Section of this Example, we also tested a full-length miRNA-21 probe directed towards the mature miRNA-21. This probe had an in situ hybridization pattern identical to the four miRNA-21 probe variants (data not shown). Data on magnification, tissue size and other information of relevance to the images, are offered in Table 3.

Conclusion

Based on the results obtained in Example 2 showing a high signal-to-noise ratio for miRNA-21 probe variants and no miRNA-210 signal, we conclude that 2 M urea in the hybridization buffer enables specific analysis of individual miRNA species in routinely-fixed, paraffin-embedded specimen.

Example 3

In Situ Hybridization of miRNA in Routinely-Fixed, Paraffin-Embedded Specimen by DIG-Labeled LNA in Response to Different Urea Concentrations in the Hybridization Buffer Introduction This Example is designed to evaluate the in situ hybridization signal of miRNA in the presence and in the absence of urea in the pre-hybridization and hybridization buffers.

Methods

Mounting of tissue sections on solid support; deparaffination; the in situ hybridization procedure including the prehybridization step; and dehydration were done as described in the Methods Section of Example 1 with the two exceptions. The first exception was that in situ hybridization buffers were tested with concentrations of urea of zero or 2 M. The second exception was that the hybridization temperature was 55° C. Detection; image analysis; and data presentation were done as described in the General Methods Section.

Specimens.

Serial sections of human colon cancer tissue from the source identified in Table 1 were prepared as described in Example 1.

Probes.

A double digoxigenin-labeled, LNA-enhanced probe for miRNA-126 (Seq-ID No 6 in Table 2) designed by Exiqon, Denmark, were used at a concentration of 40 nM.

Results

FIG. 3 shows the results of miRNA-126 ISH detection in response to zero and 2 M concentrations of urea in the pre-hybridization and hybridization buffers. In the presence of 2 M urea, a high signal-to-noise ratio indicating specific in situ hybridization of miRNA-126 was identified in vessels (a few examples of positive signals are marked by arrows on panel). Non-specific signal was prevalent in the epithelium (marked by stars on the figure). No miRNA-126 in situ hybridization was detectable in experiments leaving out urea in the pre-hybridization and hybridization buffers. A dose-response experiment was designed to establish which urea concentration provided the most optimal miRNA in situ hybridization condition. The following urea concentrations were tested: 0.5 M; 1.0 M; 2.0 M; 3.0 M; and 4.0 M. The results (not shown) showed that a significant reduction of the non-specific signal was observed at 4 M urea. The best signal-to-noise ratio (i.e., the best performance) for miRNA-126 detection was observed in the presence of 2M urea where virtually no unspecific hybridization was observed whereas at the same time, a high specific signal was obtained. Data on magnification, tissue size and other information of relevance to the images, are offered in Table 3.

Conclusion

Example 3 shows that the best in situ hybridization signal of the miRNA-126 probe is obtained when prehybridization and hybridization is carried out in the presence of 2 M urea. No signal was detectable in the absence of urea. We conclude that urea is a critical component in the prehybridization and hybridization buffers detailed in the Methods section of Example 1 (Steps 5-6), to obtain a miRNA ISH signal.

Example 4

Efficiency of In Situ Hybridization of miRNA in Routinely-Fixed, Paraffin-Embedded Specimen by DIG-Labeled LNA Probes as a Function of the Hybridization Temperature in the Presence of 2 M Urea Introduction The signal-to-noise ratio of in situ detection of miRNA is temperature-dependent. In Example 4, in situ hybridization of miRNA is examined at two temperatures to identify which one is most optimal in the presence of 2 M urea in the in the pre-hybridization and hybridization buffers.

Methods

Mounting of tissue sections on solid support; deparaffination; the in situ hybridization procedure including the prehybridization step; and dehydration were done as described in the Methods Section of Example 1 with the single exception that the hybridization temperature was adjusted to 48° C. or 55° C. Detection; image analysis; and data presentation were done as described in the General Methods Section.

Specimens.

Serial sections of human colon cancer tissue from the source identified in Table 1 were prepared as described in Example 1.

Probes.

Double digoxigenin-labeled, LNA-enhanced probes for miRNA-21 (Seq-ID No 1 in Table 2) and miRNA-126 (Seq-ID No 6 in Table 2) designed by Exiqon, Denmark, were used at a final concentration of 40 nm.

Results

FIG. 4 illustrates miRNA-21 (Panels c-d) and miRNA-126 (Panels a-b) in situ hybridization at 48° C. and 55° C. in the presence of 2 M urea in the hybridization buffer. Strong in situ hybridization signals for miRNA-21 in tumor stroma (indicated by arrows on the figure) and miRNA-126 in vessels were observed in sections hybridized at 55° C. In contrast, a non-specific signal was evident over cancer cell structures (marked by stars on the figure) at 48° C. Of the two hybridization temperatures tested in Example 4, the best signal-to-noise ratio for in situ miRNA hybridization was obtained at 55° C. Data on magnification, tissue size and other information of relevance to the images, are offered in Table 3.

Conclusion

Based on the results of Example 4, we conclude that miRNA detection in routinely-fixed, paraffin-embedded specimen by in situ hybridization in the presence of 2 M urea in the hybridization buffer is temperature dependent and should be optimized for any specific miRNA/probe combination.

Example 5

In Situ Hybridization of miRNA in Routinely-Fixed, Paraffin-Embedded Specimen by DIG-Labeled LNA Probes is Improved by Replacing the Conventional, Teratogenic Compound Formamide in the Hybridization Buffer with the Non-Toxic Compound Urea Methods Mounting of tissue sections on solid support; deparaffination; the in situ hybridization procedure including the prehybridization step; and dehydration were done as described in the Methods Section of Example 1, with the following exceptions: the hybridization temperature was 55° C.; and in addition to miRNA ISH-detection in the presence of 2 M urea in the pre-hybridization and hybridization buffers as described in the Methods section of Example 1, miRNA detection was also carried out using in situ hybridization buffers where urea was replaced by 25% or 50% formamide, as detailed in the Results section. Detection; image analysis; and data presentation were done as described in the General Methods Section.

Specimens.

Serial sections of human colon cancer tissue from the source identified in Table 1 were prepared as described in Example 1.

Probes.

Double digoxigenin-labeled, LNA-enhanced probes for miRNA-21 (Seq-ID No 1 in Table 2) and miRNA-126 (Seq-ID No 6 in Table 2) designed by Exiqon, Denmark, were used at a final concentration of 40 nm.

Results

FIG. 5 shows miRNA-21 (Panels b,d,f) and miRNA-126 (Panels a,c,e) in situ hybridization at 55° C. in the presence of either 25% urea, 25% formamide or 50% formamide in the prehybridization and hybridization buffers. The miRNA-21 and miRNA-126 in situ hybridization signals were strong in the urea-based buffer system, whereas when using formamide buffers at otherwise identical experimental conditions, low signal intensities were obtained for both miRNA-species. An experiment was designed to evaluate whether lowering of the hybridization temperature would improve the miRNA in situ hybridization signals in the presence of formamide. The results showed that decreasing the hybridization temperature from 55° C. to 48° C. did not improve the signal-to-noise ratio in the presence of formamide (data not shown). We noted in fact that although a stronger signal for specific miRNA hybridization was obtained at 48° C. in the presence of 50% formamide, the background signal (noise) also increased under these experimental conditions, eliminating the advantage of the stronger signal for specific binding (data not shown). Data on magnification, tissue size and other information of relevance to the images, are offered in Table 3.

Conclusion

Based on the results of Example 5, we conclude that miRNA detection in routinely-fixed, paraffin-embedded specimen by in situ hybridization is surprisingly much better in the presence of 2 M urea as compared to when the in situ hybridization is carried out in the presence of formamide.

Example 6

Specific In Situ Hybridization of miRNA in Routinely-Fixed, Paraffin-Embedded Specimen by DIG-Labeled LNA Probes is Enabled by Increasing the Guanidine Concentration in the Hybridization Buffer Introduction This example is designed to illustrate that specific in situ hybridization of miRNA in FFPE specimen by DIG-labeled LNA probes is enabled by the chaotroph guanidine. In addition, based on guanidine dose-response miRNA detection, the optimal concentration of guanidine in the hybridization buffer for in situ hybridization of miRNA species is identified. For the purpose of comparison, in situ hybridization of miRNA in the presence of 2 M urea was also done in this example.

Methods

Mounting of tissue sections on solid support; deparaffination; the in situ hybridization procedure including the prehybridization step; and dehydration were done as described in the Methods Section of Example 1, with two exceptions. The first exception was that a range of in situ pre-hybridization and hybridization buffers were tested with concentrations of guanidine covering 0.5 M; 1.0 M; 1.5 M and 2.0 M. The second exception was that the hybridization temperature was 55° C. In situ hybridization of miRNA in the presence of urea was done as described in Example 1 except that the hybridization temperature was 55° C. Detection; image analysis; and data presentation were done as described in the General Methods Section.

Specimens.

Serial sections of human colon cancer tissue from the source identified in Table 1 were prepared as described in Example 1.

Probes.

Double digoxigenin-labeled, LNA-enhanced probes for miRNA-126 (Seq-ID No 6 in Table 2) and miRNA-210 (Seq-ID No 9 in Table 2) designed by Exiqon, Denmark, were used at a final concentration of 40 nm.

Results

FIG. 6 shows the results of miRNA-126 detection in colon tissue by in situ hybridization at 55° C. in the presence of 2 M urea (Panel a) and various concentrations of guanidine in the pre-hybridization and hybridization buffers (Panels c-f). A specific signal for miRNA-126 is identified in vessels (indicated by arrows on the figure). Non-specific signals are prevalent in the epithelium (indicated by stars on the figure). A significant reduction of the non-specific signal was observed at the highest guanidine concentration (Panel c), whereas the intensity of the miRNA-126 specific signal is unaffected by the increasing guanidine concentration. Best performance, however, was obtained when urea was used in the pre-hybridization and hybridization buffers (Panel a), where strong in situ hybridization signals for miRNA-126 was detected and non-specific hybridization virtually eliminated. A probe targeting miRNA-210 (which is not expressed in this tissue) was tested as control in the presence of 2 M urea (Panel b). As expected, virtually no situ hybridization signal was obtained. Data on magnification, tissue size and other information of relevance to the images, are offered in Table 3.

Conclusion

We conclude that miRNA detection in routinely-fixed, paraffin-embedded specimen by in situ hybridization is enabled by using the chaotrop guanidine in the pre-hybridization and hybridization buffers. The best signal-to-noise ratio was observed in the presence of 2 M guanidine as compared to in situ hybridizations carried out at lower guanidine concentrations. It is also concluded that urea is superior to guanidine for miRNA detection by in situ hybridization because of its better performance and non-toxic nature.

Example 7

Non-Toxic, LNA-Enabled In Situ Hybridization Allows Semi-Quantitative Assessment in Routinely-Fixed FFPE Specimen Introduction Illustrated by image analysis of miRNA-21 expression this Example demonstrates that a semi-quantitative evaluation of in situ hybridization results obtained using urea in the hybridization buffer, is possible.

Methods

Mounting of tissue sections on solid support; deparaffination; the in situ hybridization procedure including the prehybridization step; and dehydration were done as described in the Methods Section of Example 1. Detection; image analysis; and data presentation were done as described in the General Methods Section. Semi-quantification of the in situ hybridization signal was done using supervised segmentation based on Bayesian classification. For miRNA-21 quantification, the miRNA species used in this Example, the following histologically stained structures were differentiated: blue areas (B) corresponded to the hybridization signal; red area (R) corresponded to the red nuclear stain (obtained with Nuclear Fast Red eg. Sigma-Aldrich cat no N3020 or GeneTex Inc., cat no GTX73305); purple areas (P) corresponded to the blue in situ hybridization signal overlaying nuclear red stain. Mucinous secretion stained with NFR (mostly observed within normal mucosa and only sporadically appearing in cancer areas) could be discriminated and was considered as background signal. The following parameters were obtained for each sample image: B, R, P, total blue (TB=B+P), total red (TR=R+P), as well as TBR=TB/TR.

Specimens.

Serial sections of human colon cancer tissue from the source identified in Table 1 were prepared as described in Example 1.

Probe.

A double digoxigenin-labeled, LNA-enhanced probe for miRNA-21 (Seq-ID No 1 in Table 2) designed by Exiqon, Denmark, was used at a final concentration of 40 nm.

Results

Illustrated by image analysis of miRNA-21 in situ hybridization in colon cancer tissue, FIG. 7. Illustrate the semi-quantitative ISH exemplified by the image sampling and image analysis of a miR-21 in situ hybridization signal in colon cancer. Panel (a) present a typical example of a whole tissue section (panel a) with normal mucosa, tumor area and submucosa after in situ hybridization for miR-21 and counterstaining with nuclear red. The tumor area is encircled and random systematically placed image positions are indicated by squared frames. Sample images are captured with a 20× objective at the systematically placed image positions. Panel (b) show one such sample image. The sample images are subsequently processed with a supervised pixel classifier which have been trained to separate the blue in situ hybridization signal from the red counter stain and the purple in situ hybridization signal overlaying the nuclear red, panel (c). Note false color red correlate to nuclear fast red in panel (b) whereas the blue ISH signal in panel (b) is shown as a green false color in panel (c). The area within the frames indicated in the lower left corner of panel (b) and (c) are in enlarged and shown in panel (d) and panel (e). Note the blue in situ hybridization signal of panel (d) appear as bright green, the purple signal of panel (d) is as yellow and the red signal of panel (d) appear as bright red in the classified image, panel (e).

Data on magnification and other information of relevance to the images, are offered in Table 3.

Conclusion

We conclude that the chromogenic stain obtained after miRNA in situ hybridization in the presence of 2 M urea in the pre-hybridization and hybridization buffers allows subsequent semi-quantitative evaluation.

Example 8

Shelf-Life for Urea-Based Hybridization Buffer for In Situ Hybridization of miRNA in Routinely-Fixed, Paraffin-Embedded Specimen Exceeds 12 Months Introduction This Example is designed to evaluate whether the storage time at 4° C. of a hybridization buffer containing 2 M urea has any impact on the in situ hybridization signal of miRNA.

Methods

Mounting of tissue sections on solid support; deparaffination; the in situ hybridization procedure including the prehybridization step; and dehydration were done as described in the Methods Section of Example 1, with the following exceptions: pre-hybridization and hybridization was carried out in buffers which were either freshly prepared (as detailed in Example 1); five months old; eight months old or 13 months old. The pre-hybridization and hybridization buffers which were not freshly prepared had been stored at 4° C. until the point of use. The miRNA-21 probe used in this experiment was diluted to a final concentration of 40 nM in the four buffers and incubated on two slides. All slides were processed for image analysis collecting 5-15 images (examples shown in the Results Section). The TB and TBR values necessary to calculate the box plots shown in FIG. 8 Panel b) were determined as described in the Methods Section of Example 7. Detection; image analysis; and data presentation were done as described in the General Methods Section.

Specimens.

Serial sections of three different human colon cancer tissues obtained from the source identified in Table 1, were prepared as described in Example 1.

Probe.

A double digoxigenin-labeled, LNA-enhanced probe for miRNA-21 (Seq-ID No 1 in Table 2) designed by Exiqon, Denmark, was used at a final concentration of 40 nm.

Results

Illustrated by image analysis of miRNA-21 in situ hybridization in colon cancer tissue, it appears from Example 8 that the urea-based buffer described in the Methods Section of Example 1, Steps 5-6, used for pre-hybridization and in situ hybridization of miRNA, is stable at 4° C. Panel A shows that a strong, highly specific miRNA-21 signal is obtained in all the buffers tested no matter whether freshly prepared, 5 months, 8 months or 13 months old (Panel A). This result is supported by the box plots of Panel B, which semi-quantitatively documents that there is no loss of miRNA ISH performance by prolonged storage of the urea-based ISH-buffer. Data on magnification, tissue size and other information of relevance to the images, are offered in Table 3.

Conclusion

We conclude that an in situ hybridization buffer containing the urea is stable at 4° C. for at least 12 months without loss of performance.

Example 9

Non-Toxic, LNA-Enabled In Situ Hybridization Allows Quantitative Assessment of Short Disease-Free Survival in Stage II Colon Cancer Patients Introduction This Experiment suggests that the level of miR-21 determined by in situ hybridization of miR-21 in routinely-fixed, paraffin-embedded specimen by DIG-labeled LNA in the presence of urea in the hybridization buffer correlates with survival probabilities for colon cancer patients.

Methods

Mounting of tissue sections on solid support; deparaffination; the in situ hybridization procedure including the prehybridization step; and dehydration were done as described in the Methods Section of Example 1. Detection; image analysis; and data presentation were done as described in the General Methods Section. Kaplan-Meier estimates of survival are presented with patients grouped in tertiles based on the miRNA-21 values. The assumption of linearity and the proportional hazards assumption were assessed using Schoenfeld and Martingale residuals.

Specimens.

Serial sections of human colon cancer tissue and sections of human rectal tissue from the source identified in Table 1 were prepared as described in Example 1.

Probe.

A double digoxigenin-labeled, LNA-enhanced probe for miRNA-21 (Seq-ID No 1 in Table 2) designed by Exiqon, Denmark, was used at a final concentration of 40 nm.

Results

FIG. 9 shows a tertile plot of Kaplan-Meier estimates of miRNA-21 in situ hybridization signal. Multivariate Cox regression analyses were performed to compare the statistical power of the observed miRNA-21 expression levels, measured as TBR values (TBR=total blue/total red) in the colon (A) and rectal (C) cancer patients and TB values (TB=total blue area) in colon cancer patients. ⅓ of the patient group with highest miRNA-21 levels (green), ⅓ of patients with intermediate miRNA-21 levels (blue), and ⅓ of the patient group with the lowest miRNA-21 levels (yellow). Data on magnification, tissue size and other information of relevance to the images, are offered in Table 3.

Conclusion

We conclude the superior performance of an in situ hybridization buffer containing the chaotropic compound urea enables quantitative assessment of the in situ hybridization signal that further allows clinical risk assessment.

Example 10

Urea-Based Hybridization Buffer Facilitates Specific In Situ Hybridization of miRNA-Species by DIG-Labeled LNA-Enhanced Probes in any Routinely-Fixed, Paraffin-Embedded Specimens Representing a Wide Range of Tissue Types Introduction Illustrated by in situ hybridization in the presence of 2 M urea of miRNA-124, miRNA-126, miRNA-145 and miRNA-205 in tissue sections from human brain, human kidney, human bowel wall and human cervix, respectively, Example 10 demonstrates that urea in the hybridization buffer enables specific analysis of individual miRNA species in routinely-fixed, paraffin-embedded specimens a wide range of tissue types.

Methods

Mounting of tissue sections on solid support; deparaffination; the in situ hybridization procedure including the prehybridization step; and dehydration were done as described in the Methods Section of Example 1. Detection; image analysis; and data presentation were done as described in the General Methods Section.

Specimens.

Serial tissue sections from routinely-fixed, paraffin-embedded specimens of human brain, colon, cervix and kidney, obtained from the sources identified in Table 1, were prepared as described in Example 1.

Probes.

Four double digoxigenin-labeled, LNA-enhanced oligonucleotides were designed by Exiqon, Denmark. The probes included a 20-mer (Seq-ID No 5 in Table 2) targeting miRNA-124; a 21-mer (Seq-ID No 6 in Table 2) targeting miRNA-126; a 23-mer (Seq-ID No 7 in Table 2) targeting miRNA-145; and a 21-mer (Seq-ID No 8 in Table 2) targeting miRNA-205. All probes were tested at a final concentration of 40 nM.

Results

FIG. 10 shows the results of in situ hybridization of four miRNA species in different types of human tissue using 2 M urea in the hybridization buffer. The four probes targeting miRNA-124 in brain (Panel a), miRNA-126 in kidney (Panel b), miRNA-145 in the bowel wall (Panel c) and miRNA-205 in cervix (Panel d) all demonstrated an intense signal. Using double digoxigenin-labeled, LNA-enhanced probes, we have also previously demonstrated in situ hybridization of miRNA-21 and miRNA-126 in colon (Examples 1 and 3) in the presence of 2 M urea in the hybridization buffer. Data on magnification, tissue size and other information of relevance to the images are offered in Table 3.

Conclusion

Based on the results obtained in Examples 2, 3 and 10, we conclude that urea in the hybridization buffer enables a non-toxic, specific in situ hybridization of individual miRNA species in a wide range of human, routinely-fixed, paraffin-embedded tissue specimens.

Example 11

Detection of β-Actin mRNA

Introduction

To illustrate that the method of the invention is applicable for most types of RNA including mRNA β-actin mRNA was detected. β-actin is a non-muscle actin that takes part in the formation of filaments comprising a major component of the cytoskeleton. Due to its general and widespread expression, β-actin expression is often used for normalization in Northern Blotting. The number of specific binding sites to β-actin mRNA be far below that of the U6 snRNA probes. Accordingly the use of β-actin as ISH normalization require a more sensitive ISH method.

Methods

Mounting of tissue sections on solid support; deparaffination; the in situ hybridization procedure including the prehybridization step; and dehydration were done as described in the Methods Section of Example 1 using 2M urea in the hybridization buffer.

Specimens

A standard FFPE specimen of human esophagus cancer The FFPE samples purchased from Proteogenex (Culver City, Calif.).

Probe

A double DIG-labelled 20 base long LNA™ probe specific to β-actin mRNA (acgaaggctcatcattcaaa (Seq ID NO 13)) LNA content 40%.

Results

This experiment show a highly specific in situ hybridization signal for human β-actin mRNA in the human esophagus cancer using an LNA probe. The signal was seen both in cancer and stroma cells. As expected the signal was cytoplasmatic localized and varied considerable between different cell typen (FIG. 11)

Conclusion

This example showed that the method of the invention provide sensitive and specific detection of β-actin mRNA in routinely formalin fixed paraffin embedded specimens.

The invention claimed is:

1. A method for detection of nucleic acids by in situ hybridization of a fixed cellular specimen comprising a hybridization step which is performed in a formamide-free, hybridization buffer that comprises a chaotropic component of either urea, salts of guanidinium, salts of guanidine, or a mixture of two or more selected from the group consisting of urea, salts of guanidinium, and salts of guanidine, wherein the nucleic acids are small, non-coding RNA molecules.

2. The method according to claim 1, wherein the cellular specimen is a formalin-fixed and paraffin-embedded (FFPE) tissue section.

3. The method according to claim 2, wherein the chaotropic component is urea.

4. The method according to claim 3, wherein the in situ hybridization utilizes a probe contains one or more LNA monomers.

5. The method according to claim 4, wherein the method comprise a hybridization step wherein said cellular specimen is contacted with a hybridization-solution comprising:
- at least one non-radioactive labelled probe comprising from 7 to 22 nucleotides which are capable of hybridizing to a specific RNA sequence and which comprise one or more LNA monomers;
- a hybrid stabilizing agent selected from the group of salts of mono- and di-valent cations; and
- urea in a concentration between 0.5 and 5 M.

6. The method according to claim 5, wherein the hybridization probe is labeled at both the 3' end and the 5' end with digoxigenin.

7. The method according to claim 6, wherein the method further comprises a step wherein a hybridization signal is visualized by formation of a dark-blue NBT-formazan precipitate, the specimens are optionally counterstained with nuclear fast red, and further comprises a quantification comprising the steps of:

taking between about 8 to about 17 random images from within the tumor area, excluding random images which do not contain evident cancer cells, excluding random images with tissue artifacts, staining artifacts, or both tissue and staining artifacts, employing a supervised segmentation based on Bayesian classification trained to recognize blue pixels areas (NBT-formazan precipitate) and, if stained with nuclear fast red, red pixel areas (nuclear fast red coloration) and purple pixel areas (both NBT-formazan precipitate and nuclear fast red coloration), to estimate the blue pixel areas (B) and, if stained with nuclear fast red, the red pixel areas (R) and purple pixel areas (P), and quantifying the relative level of the RNA by estimating either a total blue area (TB=B+P) and/or, if stained with nuclear fast red, a relative total blue area (TBR=TB/TR, wherein total red area TR=R+P wherein the TB and/or the TBR is a measurement of the specific RNA level in the sample.

8. A method of predicting a disease-free survival of a stage II colon cancer patient comprising:
a) determining a relative level of miR-21 in at least one representative tissue section from a stage II colon cancer of said patient determined by the method of claim 7,
b) comparing the relative level of miR-21 in the patient to a set of relative levels of miR-21 from a reference panel of stage II colon cancer samples of patients with known disease history, and
c) grouping the reference panel in tertiles according to the relative level of miR-21;

wherein the tertile in which the miR-21 level of said at least one representative tissue section falls is predictive of the disease-free survival probability of said patient.

* * * * *

```
                            SEQUENCE LISTING

<160> NUMBER OF SEQ ID NOS: 13

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1
tcaacatcag tctgataagc ta                                            22

<210> SEQ ID NO 2
<211> LENGTH: 15
<212> TYPE: DNA
<213> ORGANISM: Artificial Sequence
<220> FEATURE:
<223> OTHER INFORMATION: Synthetic

<400> SEQUENCE: 2
tcaacatcag tctga                                                    15

<210> SEQ ID NO 3
<211> LENGTH: 17
<212> TYPE: DNA
<213> ORGANISM: Artificial Sequence
<220> FEATURE:
<223> OTHER INFORMATION: Synthetic

<400> SEQUENCE: 3
acatcagtct gataagc                                                  17

<210> SEQ ID NO 4
<211> LENGTH: 19
<212> TYPE: DNA
<213> ORGANISM: Artificial Sequence
<220> FEATURE:
<223> OTHER INFORMATION: Synthetic

<400> SEQUENCE: 4
catgagattt caacagtca                                                19

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ggcattcacc gcgtgcctta                                               20

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
gcattattac tcacggtacg a                                             21
```

<210> SEQ ID NO 7
<211> LENGTH: 23
<212> TYPE: DNA
<213> ORGANISM: Artificial Sequence
<220> FEATURE:
<223> OTHER INFORMATION: Synthetic

<400> SEQUENCE: 7
agggattcct gggaaaactg gac                                            23

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
agactccggt ggaatgaagg a                                              21

<210> SEQ ID NO 9
<211> LENGTH: 15
<212> TYPE: DNA
<213> ORGANISM: Artificial Sequence
<220> FEATURE:
<223> OTHER INFORMATION: Synthetic

<400> SEQUENCE: 9
gctgtcacac gcaca                                                     15

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
ttcaaaacat gaattgctgc tg                                             22

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
gtgtaacacg tctatacgcc ca                                             22

<210> SEQ ID NO 12
<211> LENGTH: 22
<212> TYPE: DNA
<213> ORGANISM: Artificial Sequence
<220> FEATURE:
<223> OTHER INFORMATION: Synthetic

<400> SEQUENCE: 12
cacgaatttg cgtgtcatcc tt                                             22

<210> SEQ ID NO 13
<211> LENGTH: 20
<212> TYPE: DNA
<213> ORGANISM: Artificial Sequence
<220> FEATURE:

-continued

```
<223> OTHER INFORMATION: Synthetic

<400> SEQUENCE: 13
acgaaggctc atcattcaaa                                               20
```